US012788497B2

(12) United States Patent
Fouts et al.

(10) Patent No.: US 12,788,497 B2
(45) Date of Patent: Nov. 10, 2026

(54) POINTER TOOL FOR ENDOSCOPIC SURGICAL PROCEDURES

(71) Applicant: Stryker Corporation, Kalamazoo, MI (US)

(72) Inventors: Brian Fouts, Morgan Hill, CA (US); Aric Josef Beikmann, San Jose, CA (US); Cole Kincaid Hunter, Helena, MT (US); Lina Gurevich, Vancouver (CA)

(73) Assignee: Stryker Corporation, Portage, MI (US)

( * ) Notice: Subject to any disclaimer, the term of this patent is extended or adjusted under 35 U.S.C. 154(b) by 38 days.

(21) Appl. No.: 18/301,167

(22) Filed: Apr. 14, 2023

(65) Prior Publication Data

US 2023/0329805 A1 Oct. 19, 2023

Related U.S. Application Data

(60) Provisional application No. 63/363,106, filed on Apr. 15, 2022.

(51) Int. Cl.
*A61B 34/20* (2016.01)

(52) U.S. Cl.
CPC ...... *A61B 34/20* (2016.02); *A61B 2034/2055* (2016.02); *A61B 2034/2065* (2016.02)

(58) Field of Classification Search
None
See application file for complete search history.

(56) References Cited

U.S. PATENT DOCUMENTS

2005/0201613 A1 9/2005 Mostafavi
2010/0076455 A1* 3/2010 Birkenbach ............ A61B 90/98 600/587
2011/0082460 A1 4/2011 Revie et al.
2014/0074134 A1 3/2014 Skarbnik et al.
(Continued)

FOREIGN PATENT DOCUMENTS

CN 110547873 A 12/2019
CN 112465763 A 3/2021
(Continued)

OTHER PUBLICATIONS

Cartucho et al., "An enhanced marker pattern that achieves improved accuracy in surgical tool tracking," (Nov. 10, 2021), Computer Methods in Biomechanics and Biomedical Engineering: Imaging & Visualization, vol. 10, 2022—Issue 4. (Year: 2021).*
(Continued)

*Primary Examiner* — Keith M Raymond
*Assistant Examiner* — Ashish S. Jasani
(74) *Attorney, Agent, or Firm* — Morrison & Foerster LLP

(57) ABSTRACT

A tool for use in endoscopic surgical procedures includes a shaft, wherein the shaft includes a first end, a second end, and a first axis; and a pointer at the first end of the shaft, wherein the pointer includes: a tip located on the first end of the pointer, and a plurality of fiducial markers disposed on the pointer, wherein at least one of the fiducial markers is disposed on a surface that extends transversely to the first axis, wherein the plurality of fiducial markers are configured for providing information for locating the tip of the pointer in an endoscopic image captured by an endoscopic imaging device.

18 Claims, 15 Drawing Sheets

(56) References Cited

U.S. PATENT DOCUMENTS

| | | | |
|---|---|---|---|
| 2018/0071032 | A1* | 3/2018 | de Almeida Barreto .................... G06T 19/006 |
| 2018/0206714 | A1 | 7/2018 | Davis et al. |
| 2018/0333207 | A1* | 11/2018 | Moctezuma De la Barrera .......... G06F 3/0484 |
| 2019/0261957 | A1 | 8/2019 | Zaslavsky et al. |
| 2019/0336242 | A1 | 11/2019 | Daon et al. |
| 2020/0242971 | A1 | 7/2020 | Wang |
| 2020/0305984 | A1 | 10/2020 | Zhao et al. |
| 2021/0192759 | A1 | 6/2021 | Lang |
| 2021/0290315 | A1 | 9/2021 | Lampert |
| 2021/0369355 | A1 | 12/2021 | Masaki |
| 2021/0386485 | A1 | 12/2021 | Schneider |
| 2025/0186162 | A1* | 6/2025 | Torrie .................... A61B 90/39 |

FOREIGN PATENT DOCUMENTS

| | | | |
|---|---|---|---|
| CN | 113192075 | A | 7/2021 |
| WO | 2011/047467 | A1 | 4/2011 |
| WO | 2017/204832 | A1 | 11/2017 |
| WO | 2019/152898 | A1 | 8/2019 |
| WO | 2021/095033 | A1 | 5/2021 |
| WO | 2021/114226 | A1 | 6/2021 |
| WO | 2021/163414 | A1 | 8/2021 |

OTHER PUBLICATIONS

Gadwe et al., "Real-Time 6DOF Pose Estimation of Endoscopic Instruments Using Printable Markers," (Dec. 12, 2018), IEEE Sensors Journal ( vol. 19, Issue: 6, Mar. 15, 2019). (Year: 2019).*

Liu et al., "Hybrid electromagnetic-ArUco tracking of laparoscopic ultrasound transducer in laparoscopic video," (Feb. 3, 2021) J Med Imaging (Bellingham) Jan. 2021;8(1):015001). (Year: 2021).*

Zhang et al., "Real-time surgical tool tracking and pose estimation using a hybrid cylindrical marker," (Mar. 24, 2017), Int J Comput Assist Radiol Surg, Jun. 2017;12(6):921-930. (Year: 2017).*

Esposito et al. "Cooperative Robotic Gamma Imaging: Enhancing US-Guided Needle Biopsy," International Conference on Medical Image Computing and Computer-Assisted Intervention, Oct. 5-9, 2015 Munich, Germany; pp. 611-618.

International Search Report and Written Opinion mailed Aug. 8, 2023, directed to International Application No. PCT/US2023/018710; 22 pages.

Invitation to Pay Fees dated Jun. 29, 2023 directed to international Application No. PCT/US2023/018710; 22 pages.

Nwoye et al. (Mar. 3, 2022) "Rendezvous: Attention Mechanisms for the Recognition of Surgical Action Triplets in Endoscopic Videos," located at https://doi.org/10.48550/arXiv.2109.03223, 23 pages.

Perez et al. "Surgical Workflow Analysis, Design and Development of an Image-Based Navigation System for Endoscopic Interventions," Workshop on Clinical Image-Based Procedures, Sep. 22, 2013, Nagoya, Japan; pp. 91-98.

Stenmark et al. (Mar. 2022). "Vision-based Tracking of Surgical Motion During Live Open-Heart Surgery," Journal of Surgical Research 271: 106-116.

Office Action dated Oct. 16, 2025, directed to EP Application No. 23 722 211.2; 4 pages.

International Preliminary Report on Patentability dated Oct. 8, 2024, directed to International Application No. PCT/US2023/018710; 12 pages.

* cited by examiner

410

| Axial | Radial | X | Y | Z |
|---|---|---|---|---|
| A (412A) | 1 | 0.221763 | 0.069937 | 0.012287 |
| | 2 | 0.221763 | 0.033297 | 0.062717 |
| | 3 | 0.221763 | 0.009926 | 0.070311 |
| | 4 | 0.221763 | -0.049358 | 0.051048 |
| | 5 | 0.221763 | -0.063802 | 0.031167 |
| | 6 | 0.221763 | -0.063802 | -0.031167 |
| | 7 | 0.221763 | -0.049358 | -0.051048 |
| | 8 | 0.221763 | 0.009926 | -0.070311 |
| | 9 | 0.221763 | 0.033297 | -0.062717 |
| | 10 | 0.221763 | 0.069937 | -0.012287 |
| B (412B) | 1 | 0.284098 | 0.069937 | 0.012287 |
| | 2 | 0.284098 | 0.033297 | 0.062717 |
| | 3 | 0.284098 | 0.009926 | 0.070311 |
| | 4 | 0.284098 | -0.049358 | 0.051048 |
| | 5 | 0.284098 | -0.063802 | 0.031167 |
| | 6 | 0.284098 | -0.063802 | -0.031167 |
| | 7 | 0.284098 | -0.049358 | -0.051048 |
| | 8 | 0.284098 | 0.009926 | -0.070311 |
| | 9 | 0.284098 | 0.033297 | -0.062717 |
| | 10 | 0.284098 | 0.069937 | -0.012287 |
| C (412C) | 1 | 0.516188 | -0.014513 | 0.012287 |
| | 2 | 0.492637 | -0.042581 | 0.062717 |
| | 3 | 0.477614 | -0.060484 | 0.070311 |
| | 4 | 0.439507 | -0.105899 | 0.051048 |
| | 5 | 0.430223 | -0.116963 | 0.031168 |
| | 6 | 0.430223 | -0.116963 | -0.031168 |
| | 7 | 0.439507 | -0.105899 | -0.051048 |
| | 8 | 0.477614 | -0.060484 | -0.070311 |
| | 9 | 0.492637 | -0.042581 | -0.062717 |
| | 10 | 0.516188 | -0.014513 | -0.012287 |
| D (412D) | 1 | 0.563940 | -0.054582 | 0.012287 |
| | 2 | 0.540388 | -0.082649 | 0.062717 |
| | 3 | 0.525366 | -0.100552 | 0.070311 |
| | 4 | 0.487259 | -0.145967 | 0.051048 |
| | 5 | 0.477974 | -0.157032 | 0.031168 |
| | 6 | 0.477974 | -0.157032 | -0.031168 |
| | 7 | 0.487259 | -0.145967 | -0.051048 |
| | 8 | 0.525366 | -0.100552 | -0.070311 |
| | 9 | 0.540388 | -0.082649 | -0.062717 |
| | 10 | 0.563940 | -0.054582 | -0.012287 |

FIG. 4B

POINTER TOOL FOR ENDOSCOPIC SURGICAL PROCEDURES

CROSS-REFERENCE TO RELATED APPLICATIONS

This application claims the benefit of U.S. Provisional Application No. 63/363,106, filed Apr. 15, 2022, the entire contents of which are hereby incorporated by reference herein.

FIELD

This disclosure relates to a pointer tool for use in endoscopic surgical procedures that includes features on the tool that allow for determining the location of a tip of the pointer tool in two or more dimensions within imaging data taken when the pointer tool is within a field of view of a medical imaging device.

BACKGROUND

Medical imaging involves the use of a high-definition camera often coupled to an endoscope inserted into a patient to provide a surgeon with a clear and precise view within the body. In many instances, the video data collected at the camera will be transmitted to a display device that will render the video data collected onto a display so that the surgeon can visualize the internal area of the body that is being viewed by the camera. In many instances, the camera can serve as the eyes of the surgeon during the surgery since the camera may provide the only view of the internal area of the patient. In many instances, the surgeon may depend on the camera to perform procedures in the internal area of the patient using one or more tools that are specifically configured to aid the surgeon as they perform the medical procedure. The surgeon can view the imaging feed being displayed to them during a surgery to manipulate the tool and to navigate the tool within the internal area of the patient.

Medical imaging data such as an endoscopic video feed and/or image can also be used by the surgeon to measure distances within the internal portion of a patient. For instance, if the scale of the image shown on the screen is known, as well as depth information, then the surgeon can use the endoscopic imaging data to measure distances of the internal portion of the patient in either two-dimensions, three-dimensions, or both. In the instance where sufficient information about an endoscopic image exists to measure distances or determine the position of an object in the image, the tools that are used in the endoscopic procedure can be used to measure distances and or determine the position of a feature in the internal area of the patient. A pointer tool is an example of a tool that can be used by a surgeon during an endoscopic procedure. A pointer tool can include a tip that the surgeon can use to palpate the anatomy of the patient, and act as the "fingers" of the surgeon during an endoscopic surgery. Thus, the surgeon can use the tip of a pointer tool to measure distance in the anatomy or otherwise determine the precise two or three dimensional location of a feature of the patient's anatomy. For instance, the end of the tip can be used to delineate two end points of a measurement. The tip of the point tool can be used to indicate a start point and an endpoint of a measurement. With respect to determining the location of a feature, the tip of the pointer tool can be placed at a feature of interest, and the position of the tip can be recorded.

However, in order to use the pointer in the manner described above, the endoscopic imaging system, and more specifically the device processing the imaging data must be able to recognize the location of the tip in the endoscopic imaging data. The imaging data can be represented by a plurality of digital pixels, and thus in order to determine the tip of the tool in the image, the device must first determine the presence of the pointer tool in the imaging data, and then determine the exact pixels that are associate with the tip of the pointer tool. Determining the position of the tip can be challenging in its own right, but this challenge can be made even more complex and difficult to overcome when the tip gets obscured or hidden from the view of the camera during the surgical procedure. For instance, if the tip gets buried in the anatomy of the patient such that it is not visible in the endoscopic images, then determining its two or three dimensional position can be difficult.

SUMMARY

Disclosed herein is a pointer tool that is configured to help an imaging analysis device/process determine the location of the tip in two or three dimensions using medical imaging data. In one or more examples, the pointer tool can include a shaft that on one end includes a pointer. In one or more examples, the pointer includes a first portion that is axially aligned with the shaft, and a second portion that is oriented angularly with respect to the shaft. In one example, the pointer includes a tip located on the distal end of the pointer. In one or more examples, the pointer includes one or more sets of fiducial markers, wherein each fiducial marker can be used to determine location information regarding the tip of the pointer. In one or more examples, the fiducial markers can include one or more ArUco markers. The ArUco makers can be configured to be identified in an endoscopic image, and can be used to determine the location of the tip in two dimensional or three dimensional space.

In one or more examples, the sets of ArUco markers can include ArUco markers disposed on faces of one or more fiducial rings. In one or more examples, the ArUco markers can be used to identify the locations of features of the ArUco markers, features of the fiducial rings, and/or of other features of the tool. The systems and methods can use the features to then determine the location of the tip by accessing a look-up table which provides geometric relationships between the features and the tip. Thus, the ArUco markers can be used to identify the location of the features for determining the position of the tip.

In one or more examples, a tool, such as for use in endoscopic surgical procedures, comprises: a shaft, wherein the shaft includes a first end, a second end, and a first axis, a pointer at the first end of the shaft, wherein the pointer comprises: a tip, and a plurality of fiducial markers disposed proximally of the tip, wherein at least one of the fiducial markers is disposed on a surface that extends transversely to the first axis, wherein the plurality of fiducial markers are configured for providing information for locating the tip of the pointer in an endoscopic image captured by an endoscopic imaging device.

Optionally, the shaft and the pointer are machined from a single piece of material.

Optionally, the pointer is generated using an injection molding process, and wherein the pointer is attached to the shaft.

Optionally, the pointer is over-molded onto the shaft.

Optionally, the plurality of fiducial markers are ArUco markers.

Optionally, each fiducial marker is disposed on a face of a first fiducial ring.

Optionally, each fiducial marker is configured to identify the fiducial marker.

Optionally, the pointer comprises a first portion that is axially aligned with the first axis of the shaft; and a second portion aligned with a second axis that is oriented angularly with respect to the first axis of the shaft.

Optionally, the pointer comprises at least one fiducial ring that comprises the plurality of fiducial markers.

Optionally, the pointer comprises first and second fiducial rings.

Optionally, the first and second fiducial rings are spaced apart from the tip of the pointer.

Optionally, the plurality of fiducial markers disposed on the first and second fiducial rings are ArUco markers.

Optionally, each ArUco marker is disposed on a face of the at least one fiducial ring.

Optionally, each ArUco marker comprises a unique identifier that can be used to obtain a distance between one or more features of the fiducial marker and the tip.

Optionally, the pointer comprises a first set of fiducial markers spaced apart from a second set of fiducial markers.

Optionally, the first set of fiducial markers is axially aligned with the first axis of the shaft.

Optionally, the second set of fiducial markers is aligned with a second axis that is oriented angularly with respect to the first axis of the shaft.

Optionally, the tool comprises a controller disposed on the second end of the shaft, and wherein the controller is configured to receive one or more inputs from a user of the tool.

Optionally, the controller comprises one or more buttons that are configured to be pushed by a user to indicate a user's desired action.

Optionally, the buttons are configured to allow a user to navigate a graphical user interface displayed on an external display.

Optionally, the controller comprises a printed circuit board.

Optionally, the controller is configured to provide a message through a cable to an external computing system identifying the tool to the external computing system.

Optionally, the controller is configured to wirelessly communicate with an external computing system.

Optionally, the controller communicates wirelessly with the external communication system using a pre-defined wireless transmission standard.

Optionally, the tool comprises an interface component attached to the second distal end of the shaft, and wherein the interface component is configured to interface with an external controller.

Optionally, the tool comprises a memory configured to identify the tool to the external controller.

Optionally, the tool comprises a memory configured to identify the tool to the external computing system.

Optionally, at least a portion of the pointer is part of the shaft.

In one or more examples, a method for determining the three dimensional location of a tip of a tool in an image, such as in an endoscopic image, comprises: receiving an image, such as an endoscopic image, wherein the (e.g., endoscopic) image comprises an image of the tool, optionally, wherein the tool comprises any of the tools described above; determining an identity of at least one fiducial marker of a plurality of fiducial markers of the tool; and determining a, for example three-dimensional, location of the tip of the tool based on the determined identity of the at least one fiducial marker.

Optionally, the method includes determining locations of corners of the at least one fiducial marker of the plurality of fiducial markers in the received endoscopic image, wherein the three-dimensional location of the tip of the tool is determined based on the locations of the corners.

Optionally, determining an identity of the at least one fiducial marker of the plurality of fiducial markers comprises: determining the location of the at least one fiducial marker in the received endoscopic image, determining one or more visual patterns of the at least one fiducial marker, and extracting the identity of the at least one fiducial marker based on the one or more visual patterns.

Optionally, determining the three-dimensional location of the tip of the tool based on the determined identity of the at least one fiducial marker comprises: identifying at least one corner of a plurality of corners of the at least one fiducial marker, and determining a three-dimensional location of the at least one corner of the plurality of corners relative to the tip.

Optionally, determining the three-dimensional location of the at least one corner of the plurality of corners relative to the tip comprises: accessing a look-up table comprising a list of the plurality of fiducial markers and a corresponding plurality of corners, wherein each entry pertaining to a corner in the look-up table comprises a three-dimensional location of the respective corner relative to the tip, and extracting the three-dimensional location of the at least one corner relative to the tip.

Optionally, the three-dimensional location of the tip of the tool is determined based on the determined three-dimensional location of the at least one corner of the plurality of corners relative to the tip.

Optionally, the tool comprises a first set of fiducial markers arranged on a first fiducial ring and a second set of fiducial markers arranged on a second fiducial ring.

Optionally, the first and second sets of fiducial markers are spaced apart from the tip of the pointer.

Optionally, the first set of fiducial markers is disposed on a first portion of the pointer that is axially aligned with a first axis of the shaft.

Optionally, the second set of fiducial markers is disposed on a second portion of the pointer that is aligned with a second axis that is oriented angularly with respect to the first axis of the shaft.

Optionally, the plurality of fiducial markers are ArUco markers.

Optionally, the method comprises applying one or more machine learning models to the received endoscopic image if an identity of the plurality of fiducial markers cannot be determined.

Optionally, the method includes applying one or more machine learning models to the received endoscopic image to determine the location of the first fiducial marker in the received endoscopic image.

Optionally, determining the location of the tip of the tool comprises: applying one or more machine learning models to the received endoscopic image to segment the tool from the received endoscopic image, and determining the location of the tip of the tool based on the determined identity of the first fiducial marker and the segmented tool from the received endoscopic image.

In one or more examples, a system for determining the three dimensional location of a tip of a tool in an endoscopic image comprises: a memory, one or more processors, wherein the memory stores one or more programs that when executed by the one or more processors, cause the one or more processors to perform any of the methods described above In one or more examples, a non-transitory computer readable storage medium stores one or more programs for execution by one or more processors of a computing system for performing any of the methods described above.

It will be appreciated that any of the variations, aspects, features, and options described in view of the systems apply equally to the methods and vice versa. It will also be clear that any one or more of the above variations, aspects, features, and options can be combined.

BRIEF DESCRIPTION OF THE FIGURES

The invention will now be described, by way of example only, with reference to the accompanying drawings, in which:

FIGS. 4A and 4B illustrate an exemplary placement of one or more fiducial rings of the pointer tool and corresponding tip locations according to examples of the disclosure.

DETAILED DESCRIPTION

Figure 1:
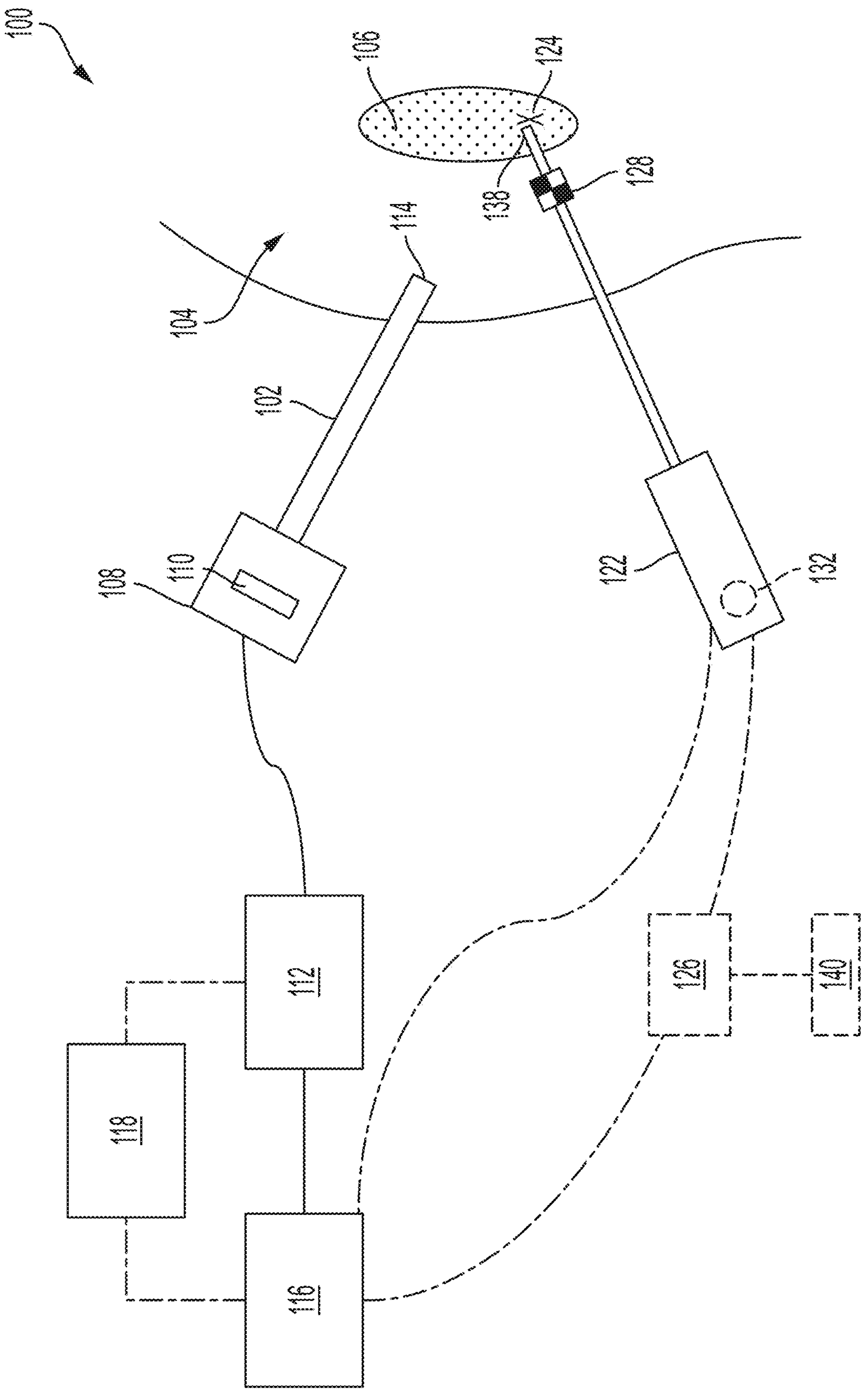
FIG. 1 illustrates an exemplary endoscopy system according to examples of the disclosure.

Reference will now be made in detail to implementations and examples of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein is a pointer tool that is configured to provide information to an image processing algorithm that can use the information to determine the two-dimensional and/or three-dimensional location of a tip of the pointer tool, for example, within the internal area of a patient during a endoscopic surgical procedure. In one or more examples, the pointer tool can include a shaft that on one end includes a pointer. In one or more examples, the pointer includes a first portion that is axially aligned with the shaft, and a second portion that is oriented angularly with respect to the shaft. In one example, the pointer includes a tip located on the distal end of the pointer. In one or more examples, the pointer includes one or more fiducial rings that has a plurality of fiducial markers disposed on them, wherein each fiducial marker is configured to provide information that can be used by an image processing algorithm to locate the tip of the pointer. In one or more examples, the fiducial markers can include one or more ArUco markers. The ArUco makers can be configured to be identified in an (e.g., endoscopic) image, and can be used to determine the location of the tip in two dimensional or three dimensional space.

In one or more examples, the ArUco markers can be disposed on a face of the fiducial rings, and each fiducial ring can have one or more corners or other geometric feature. In one or more examples, the ArUco markers can be used to identify the location of the geometric features or features of the ArUco markers. The systems and methods can use the features to then determine the location of the tip by accessing a look-up table which provides geometric relationships between the features and the tip. Thus, the ArUco markers can help to identify the location of the features of the fiducial ring and can also help to identify the position of the tip.

In one or more examples, the pointer tool can include a controller located on an end of the shaft of the pointer that is configured to allow for a user to provide input commands with the tool, for instance to indicate a start time to initiate a measurement using the pointer tool. In one or more examples, the controller of the pointer tool can be communicatively coupled to a cable interface that can be configured to provide the user inputs provided to the controller to a processing system that can process the user input to perform measurements or other procedures involving the tool. In one or more examples, the shaft can include an interface on one end of the tool that can be configured to interface with an external controller. In one or more examples, the pointer tool can include an RFID component that can be configured to identify the tool to the external controller.

In the following description of the various embodiments, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present disclosure as described herein.

FIG. 1 illustrates an exemplary endoscopy system according to examples of the disclosure. System 100 includes an endoscope 102 for insertion into a surgical cavity 104 for imaging tissue 106 within the surgical cavity 104 during a medical procedure. The endoscope 102 may extend from an endoscopic camera head 108 that includes one or more imaging sensors 110. Light reflected and/or emitted (such as fluorescence light emitted by fluorescing targets that are excited by fluorescence excitation illumination light) from the tissue 106 is received by the distal end 114 of the endoscope 102. The light is propagated by the endoscope 102, such as via one or more optical components (for example, one or more lenses, prisms, light pipes, or other optical components), to the camera head 108, where it is directed onto the one or more imaging sensors 110. In one or more examples, one or more filters (not shown) may be included in the endoscope 102 and/or camera head 108 for filtering a portion of the light received from the tissue 106 (such as fluorescence excitation light).

The one or more imaging sensors 110 generate pixel data that can be transmitted to a camera control unit 112 that is communicatively connected to the camera head 108. The camera control unit 112 generates a video feed from the pixel data that shows the tissue being viewed by the camera at any given moment in time. In one or more examples, the video feed can be transmitted to an image processing unit 116 for further image processing, storage, display, and/or routing to an external device (not shown). The images can be transmitted to one or more displays 118, from the camera control unit 112 and/or the image processing unit 116, for visualization, such as by medical personnel (such as a surgeon) for visualizing the surgical cavity 104 during a surgical procedure on a patient.

In one or more examples, the images generated by the system 100 described above can, for example, be used to create two-dimensional and/or three-dimensional maps of the internal anatomy of a patient. For instance, in one or more examples, the images are represented on a screen in two-dimensions and thus can be represented using an (x,y) coordinate system, in which each location or point in the internal portion can correspond to a specific (x,y) coordinate. Even as the camera is repositioned throughout the surgery, the images created by the camera can be stitched together to create an overall two-dimensional mapping of the internal anatomy of the patient, such that no two points in the internal anatomy of the patient viewed by the camera will have the same (x,y) coordinate.

In one or more examples, the two-dimensional model created by the endoscopic video feed during or after a surgical procedure can, for example, be transformed into a three-dimensional model by adding depth information to the two-dimensional model. In one or more examples, depth information pertaining to endoscopic image or endoscopic video feed can be obtained by using hardware-based methods such as employing the use of stereo cameras, time of flight sensors, etc. Additionally or alternatively, the depth information can be acquired algorithmically, for instance by using a structure from motion process in conjunction with a camera to acquire depth information. Additionally or alternatively, the depth information can be acquired using external data acquired on the patient such as magnetic resonance images (MRIs), etc. Similar to two-dimensional mappings, the above techniques can be employed to create a three-dimensional map of the internal anatomy of the patient, such that every point visualized by an endoscopic camera can have a unique (x,y,z) coordinate.

The two and/or three-dimensional mappings discussed above can be used to generate two or three dimensional measurements within the internal portion of the patient. For instance, the distance between two (x,y,z) points within the patient's internal anatomy can be measured in real-time using the three-dimensional mappings acquired using the systems and processes described above. In order to take a measurement, a surgeon may need to accurately identify the start point and end point of such a measurement, and/or the contours of the measurement to be taken. In one or more examples, a surgeon can, for example, utilize a pointer tool 122 to point to the specific points in the internal anatomy of a patient to use in a two or three-dimensional measurement that is being taken using images taken from an endoscopic imaging device. In one or more examples, the pointer tool 122 can include a pointer that has a tip 138 located at an end of the pointer tool 122 that can be captured in imaging data generated by the camera head 108 and used by the surgeon to mark or point to a specific point of interest 124 in the imaging data of the patient's internal anatomy. One challenge associated with using a pointer tool to mark points in a patient's anatomy is identifying the precise location of the tip in the endoscopic image.

In order to use the pointer as a "marking" device, the image processor (that maps two and three-dimensional points in a patient's anatomy to a two/three-dimensional model of the patient's anatomy) must determine where the tip of the pointer being used to mark is precisely located. The task of finding the tip of the pointer tool can be even more complicated when the tip is obscured by a patient's anatomy (for instance by being buried in the patient's tissue) or otherwise not completely visible in the endoscopic image due to other occlusions or obfuscations. To this end, pointer tool 122 can be specifically configured to allow for easy and robust identification of the tip 138 of a pointer tool by an image processing system, such as image processing unit 116, for the purposes of marking a portion of a patient's anatomy or any other context in which the precise two and/or three-dimensional location of the tip may be required. The pointer tool 122 can include multiple features that collectively enable an image processing system to acquire the precise location of the tip 138 regardless of the orientation the pointer tool 122 is in, and regardless of whether the tip 138 is visible in the image or not. For example, the pointer tool 122 can include one or more fiducial markers 128 that can be captured in imaging data and used by an image processing system, such as image processing unit 116, to not only identify the pointer tool 122, but identify its orientation and identify the precise two or three-dimensional location of the tip of the tool, which the image processing system can use to take two or three-dimensional measurements.

In some examples, the pointer tool 122 can include one or more buttons 132 or other user interface that a user can use to instruct the image processing unit 116 to determine the position of the location of interest 124 based on the position of the tip 138 of the pointer tool 122. For example, the user can position the pointer tool 122 at or near the location of interest 124 and press the button 132 on the pointer tool 122 to indicate that the image processing unit 116 should determine the position of the location of interest 124. The pointer tool 122 can be directly connected to the image processing unit 116 or can be connected to a tool controller 126 configured to receive input from the pointer tool 122. The tool controller 126 can receive a signal from the pointer tool 122 responsive to a button press. The tool controller 126 can send a notification to the image processing unit 116 indicative of the user's instruction to determine the location of interest 124. The image processing unit 116 can then analyze one or more endoscopic images to determine the three-dimensional position of the location of interest 124. The user can reposition the pointer tool 122 and provide another button press to control the system 100 to determine a new location of interest based on the repositioned position of the pointer tool 122. This can be repeated any number of times by the user. In some examples, the pointer tool 122 may include a memory storing identifying information for the pointer tool 122 that the pointer tool 122 may provide to the image processing unit 116 and/or the tool controller 126 so that the imaging processing unit 166 and/or the tool controller 126 can determine how to interpret communications from the pointer tool 122.

In some examples, the pointer tool 122 does not include any user input features. Instead, the pointer tool 122 may include a shaft extending from a simple handpiece or simply a shaft grasped at one end by a user. In such examples, a user input instructing the image processing unit 116 to determine the three-dimensional position of the location of interest 124 can be provided via any other user interface of system 100, including, for example, a voice control system, a remote control, another tool, or a foot switch. For example, the tool controller 126 may include or be connected to a user interface 140, such as a foot switch, to which a user may provide an input to instruct the image processing unit 116 to determine the three-dimensional position of the location of interest 124. Optionally, the tool controller 126 and user interface 140 can be used to communicate with tools other than the pointer tool 122, such as a cutting tool, and the tool controller 126 can change how it responds to inputs to the user interface 140 based on which tool is being used. The image processing unit 116 may detect the presence of the pointer tool 122 in imaging data, such as by detecting the fiducial marker 128, and may inform the tool controller 126 that the pointer tool 122 is being used. The tool controller 126 may then respond to inputs to the user interface 140 based on configuration data associated with the pointer tool 122 (instead of, for example, configuration data associated with a cutter). Optionally, the configuration data may be customizable based user preferences so that, for example, mappings of user interface 140 inputs to tool controller 126 outputs can be different for different users.

Figure 2:
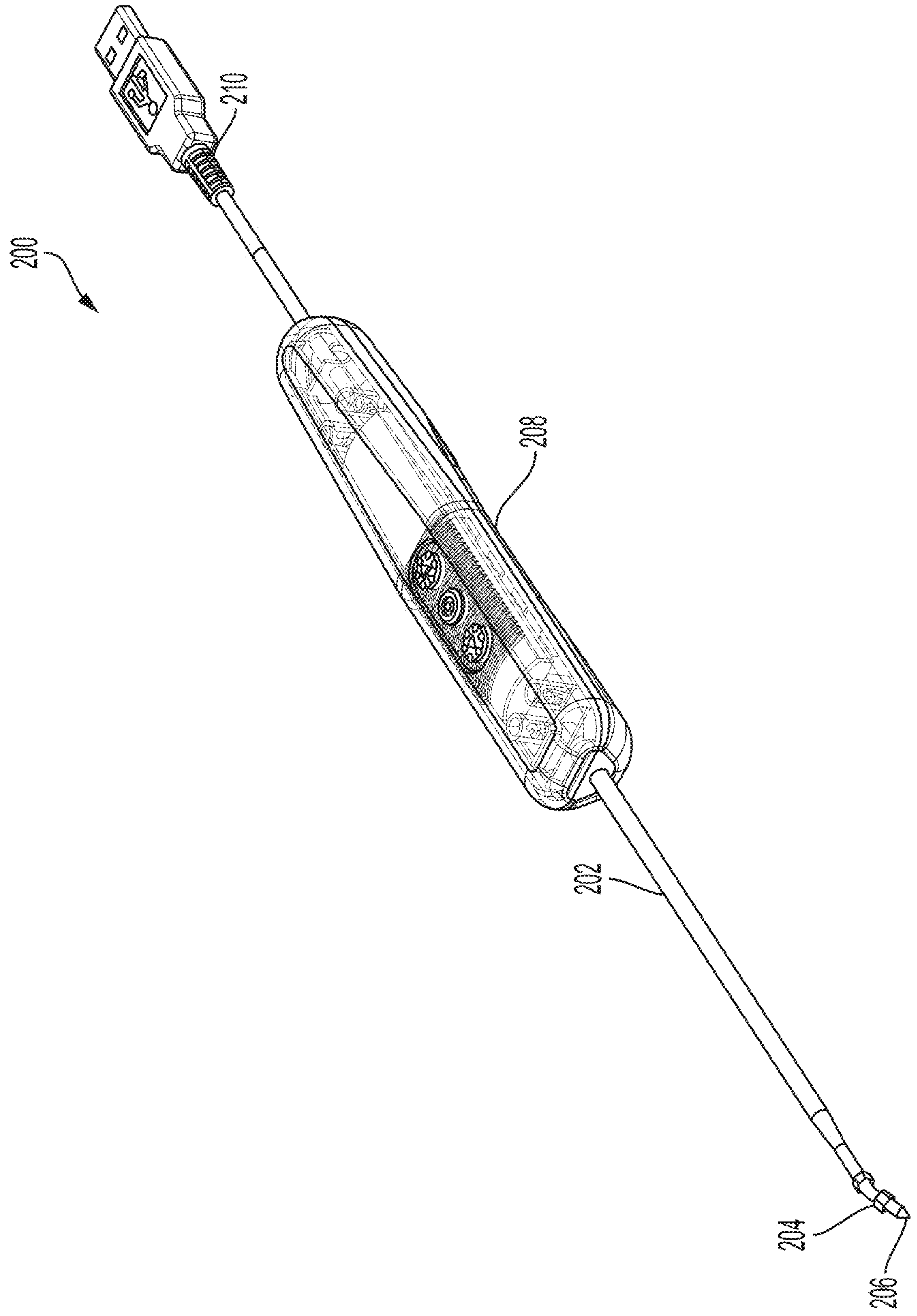
FIG. 2 illustrates an exemplary pointer tool according to examples of the disclosure.

FIG. 2 illustrates an exemplary pointer tool that can be used for pointer tool 122 of FIG. 1, according to examples of the disclosure. In one or more examples, the pointer tool 200 of FIG. 2 can include a shaft 202. In one or more examples, the shaft 202 can be a body of a pre-determined length that can be long enough to be inserted into an internal area of a patient during a minimally invasive surgical procedure, and long enough to allow for the surgeon to interact and manipulate the internal anatomy of the patient during the procedure. In one or more examples (and as described in further detail), the shaft 202 of the pointer tool 200 can be formed from a single piece of rigid machine metal such as aluminum or stainless steel. In one or more examples, a less rigid material can be used such as a thermoplastic.

In one or more examples, the pointer tool 200 can include a pointer 204 which can be located on one end of the shaft. In one or more examples, the pointer 204 can refer to a plurality of features located on the end of the shaft 202 that include a tip 206 that can be used by the surgeon to mark points in the internal portion of the patient's anatomy during a minimally invasive surgical procedure. As will be described in further detail below, the pointer 204 can also include a plurality of features and can be shaped in manner that can aid an image analysis tool or computer vision tool in acquiring the two-dimensional and/or three-dimensional location of the tip 206 in an endoscopic image. In one or more examples, the pointer 204 can be part of the shaft 202 (i.e., the shaft 202 and the pointer 204 are part of the same body), or alternatively, in or more examples, the pointer 204 (including the features of the pointer) can be formed as a separate component that is then adhered to the shaft 202. For instance, in one or more examples, the pointer 204 can be made using an injection molding process using a thermoplastic that can be press fit to the shaft 202. In one or more examples, the tip 206 can be over-molded to the shaft to give the pointer 204 additional structural reinforcement.

In one or more examples, the pointer tool 200 can include a controller 208 that is located on an end of the shaft opposite to the end where the pointer 204 is disposed. In one or more examples, the controller 208 (described in further detail below) can include a plurality of components configured to accept an input from the user. For instance, in one or more examples, the controller 208 can be configured to allow for the user to indicate the starting points and end points of a measurement to be taken using point. Thus, in one or more examples, when a user engages a button on the controller, an image processing or computer vision process that is used to take the measurement can determine the location of the tip 206 of the pointer 204, and can track the motion of the tip, until the user engages the same or another button on the controller 208 indicating the end of the measurement. In one or more examples, the controller 208 can be used to facilitate user inputs to an external controller and/or display that the pointer tool 200 is communicatively coupled to. Thus, in one or more examples, the controller 208 is not limited to operations involving the pointer 204 of the pointer tool 200 and can be generally used to facilitate interaction between a user and a computing device in much the same way that a mouse or keyboard would.

In one or more examples, the pointer tool 200 can also include a cable assembly 210 that is connected to the controller 208 and is configured to transmit electronic messages/inputs or other data processed by controller 208 to an external device, such as image processing unit 116 (directly or via one or more intermediate computing systems). In one or more examples, the cable assembly 210 can be configured to transmit messages using one or more varieties of communications protocols/standards including universal serial bus (USB) or any other interface protocol that can carry communications from the controller to an external power device as well as provide any needed power to the controller 208. Alternatively, the controller 208 can be powered using an internal battery.

In one or more examples, the pointer 204 of the pointer tool 200 can be configured to include one or more fiducial markers, which can be captured in endoscopic images and used by an image processing system, such as image processing unit 116, to locate the precise location of the tip 206 of the pointer 204. In one or more examples, the pointer 204 can be configured so that at least one fiducial marker (whose operation is described in further detail below) can be visible to the endoscopic camera no matter the orientation of the pointer tool 200 in relation to the camera that is being used to view the pointer tool in the internal portion of the patient during a minimally invasive procedure.

Figure 12A:
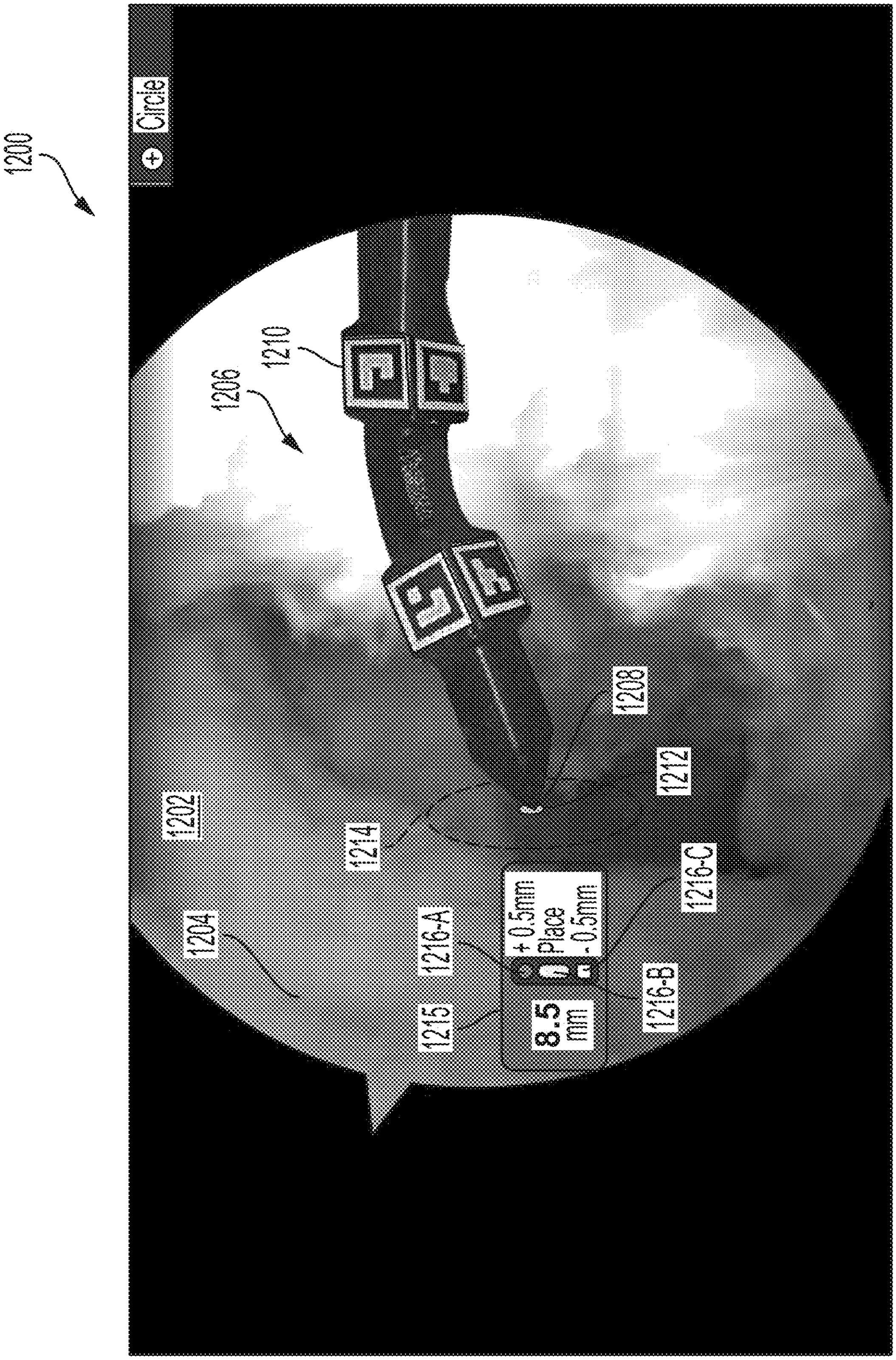
FIGS. 12A-C illustrate an exemplary graphical user interface (GUI) that may be interacted with using a pointer tool according to examples of the disclosure.
Figure 12B:
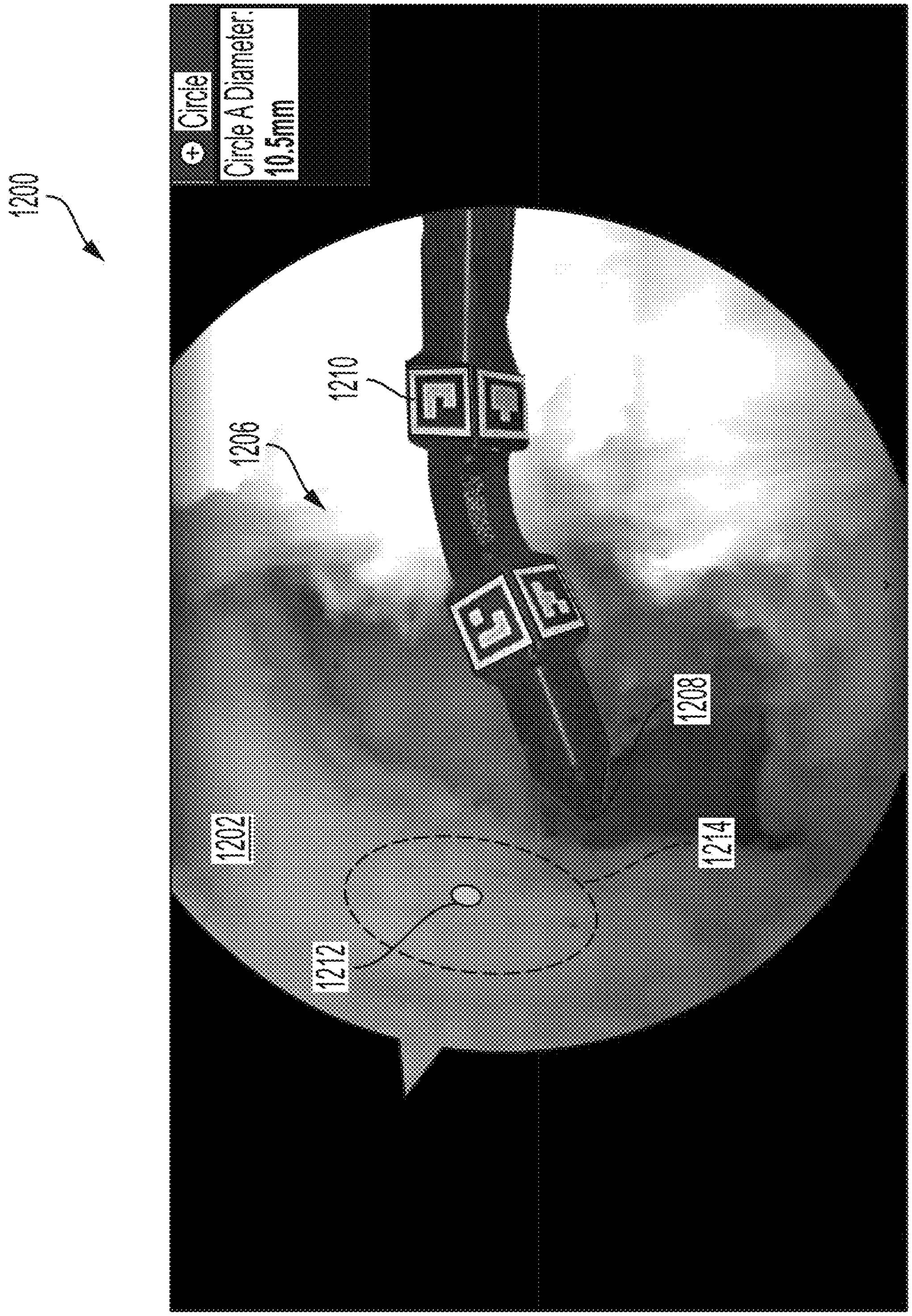
Figure 12C:
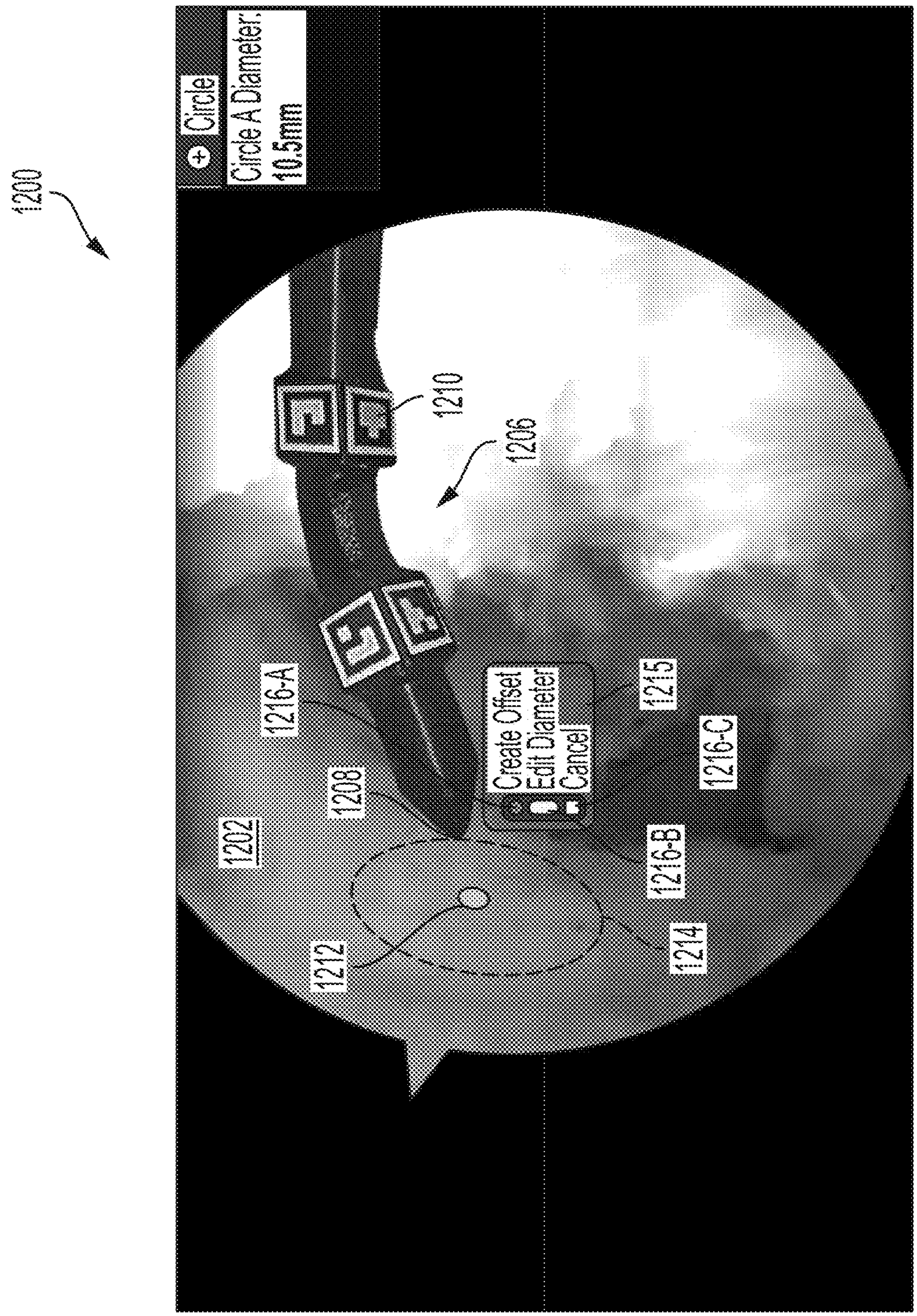

An example of the use of a pointer tool for facilitating interaction between a user and a computing device is illustrated in FIGS. 12A-C, which illustrate an exemplary graphical user interface (GUI) 1200 that may be generated by image processing unit 116 and displayed on display 118 during a surgical procedure. GUI 1200 may include an endoscopic video 1202 that captures tissue of interest 1204 and a pointer tool 1206, which can be any of the pointer tools described herein. A user may provide a user input to a user interface of the pointer tool 1206, such as a button press to a button of the pointer tool 1206, to instruct the image processing unit 116 to locate the tip 1208 of the pointer tool 1206 based on one or more fiducial markers 1210 of the pointer tool 1206 that are visible in the endoscopic video 1202. In response to such a user input, a location indicator 1212 for the located tip 1208 may be displayed by the image processing unit 116 in the GUI 1200 as an overlay on the endoscopic video 1202. Optionally, a region graphical indicator 1214 may also be displayed, such as to indicate how a hole to be drilled at the location of the tip 1208 may look, e.g., hole dimensions and/or trajectory. A function guide 1215 may be displayed that provides options for a user to interact with the GUI 1200. The function guide 1215 may include button icons 1216-A, 1216-B, 1216-C that correspond to buttons of the pointer tool (see, for example, buttons 806 of FIG. 8). Alongside the button icons 1216-A, 1216-B, 1216-C are indications of what actions may be performed in response to pressing the respective buttons. For example, pressing a button associated with button icon 1216-B will place the location indicator 1212 and region graphical indicator 1214 at the current location of the tip 1208 of the pointer tool 1206 within the endoscopic video 1202 and pressing a button associated with button icon 1216-A will increase the size of the region graphical indicator 1214 by 0.5 mm.

FIG. 12B illustrates the placement of the location indicator 1212 and region graphical indicator 1214 resulting from the user pressing the button associated with button icon 1216B of FIG. 12A. The user can reposition the pointer tool 1206 and the location indicator 1212 and region graphical indicator 1214 will remain in place within the endoscopic video 1202. The user could, for example, reposition the pointer tool 1206 to a new location and use the buttons of the pointer tool 1206 to command the generation of a measurement from the new location to the location where the location indicator 1212 was placed.

The image processing unit 116 can track the location of the tip 1208 of the pointer tool 1206 based on the one or more fiducial markers 1210, enabling the image processing unit 116 to determine where the tip 1208 of the pointer tool 1206 is at any given time. Based on this knowledge, the image processing unit 116 can automatically respond to particular positioning of the tip 1208 of the pointer tool 1206 with respect to the GUI 1200, which can enable the user to use the pointer tool 1206 to directly interact with the GUI 1200. For example, shown in FIG. 12C is an example where a user has moved the tip 1208 of the pointer tool 1206 to the region graphical indicator 1214, which the image processing unit 116 has detected and responded to by displaying function guide 1215 with options that the user can select via a corresponding button press to modify the region graphical indicator 1214. In the illustrated example, button icon 1216-A indicates that a press of the corresponding button of the pointer tool 1206 will initiate a process for creating an offset from the region graphical indicator 1214, button icon 1216-B indicates that a press of the corresponding button of the pointer tool 1206 will initiate a process for editing a diameter of the region graphical indicator 1214, and button icon 1216-C indicates that a press of the corresponding button of the pointer tool 1206 will cancel the routine (e.g., delete the placed location indicator 1212 and region graphical indicator 1214).

Figure 3:
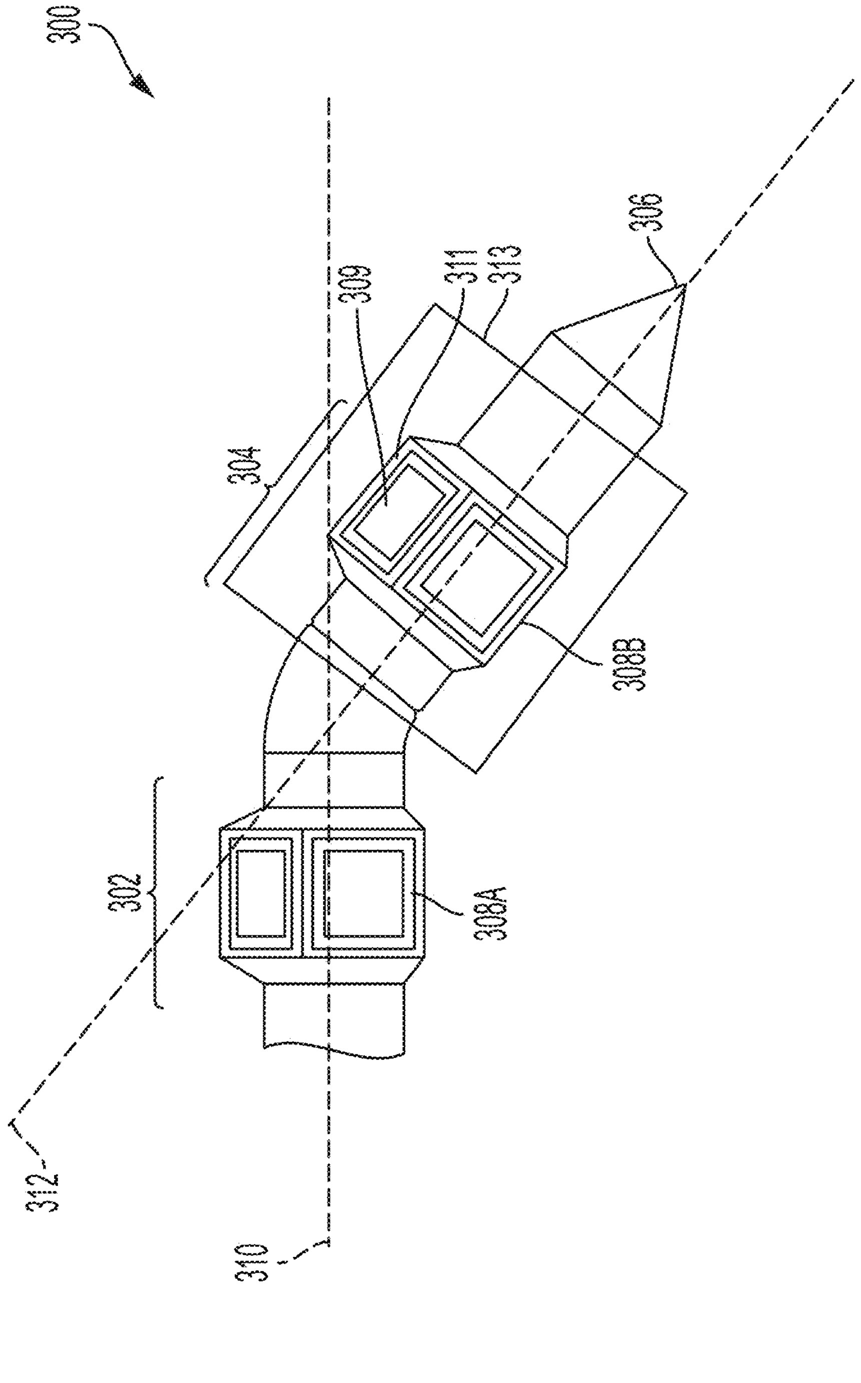
FIG. 3 illustrates an exemplary pointer of the pointer tool according to examples of the disclosure.

FIG. 3 illustrates an exemplary pointer of the pointer tool according to examples of the disclosure. In one or more examples, the pointer 300 of FIG. 3 can represent an example of the pointer discussed above with respect to pointer 204 of pointer tool 200 of FIG. 2. In one or more examples, the pointer 300 can include two portions—first portion 302 and second portion 304. First portion 302 of the pointer can be axially aligned with the shaft of the pointer tool. In one or more examples, and in the example in which the pointer and the shaft are machined from a single piece of material, the first portion of the pointer that is axially aligned with the shaft can be a distal end of the shaft and thus the first portion 302 can refer to a portion of the shaft that is located on the end of the shaft and that abuts the second portion 304 (described in further detail below). In one or more examples, and in the examples in which the pointer 300 is formed as a separate component to the shaft, the first portion 302 can be arranged (when adhered to the shaft) such that the first portion 302 is axially aligned with the shaft. Thus, in one or more examples, the first portion 302 of the pointer 300 can be aligned with axis 310, and axis 310 can be aligned with a central axis of the shaft such that the first portion 302 and the shaft are axially aligned with one another with respect to axis 310.

In one or more examples, the pointer 300 can include a second portion 304 that is aligned to a second axis that is oriented angularly with respect to the axis of the shaft and the first portion 302. As shown in FIG. 3, the second portion 304 of pointer 300 can be aligned to axis 312 which is angularly oriented to axis 310. In this way, the pointer 300 of FIG. 3 can include a "bend" in which the second portion 304 of the pointer extends transversely with respect to the first portion 302 of the pointer 300 (i.e., the longitudinal axes of the first and second portions extend transversely to one another), resulting in at least one of the fiducial markers being disposed on a plane (the plane coincident with the face on which the fiducial marker is disposed) that extends transversely to axis 310 of the shaft of the pointer 300. For example, fiducial marker 309 is disposed on a face 311 that is coincident with a plane 313 that intersects axis 310 (thus, the fiducial marker can be said to be oriented transversely to the axis 310). In one or more examples, the "bend" of the pointer 300, resulting in fiducial markers oriented transversely to an axis of the shaft of the pointer tool, can be useful to allow the surgeon to view the tip 306 of the pointer 300 during a surgical procedure, and in one or more examples, can help to ensure that at least one of a plurality of fiducial markers can be visible to a camera no matter the orientation of the pointer 300 within an internal portion of the patient during a minimally invasive surgical procedure and no matter the orientation of the camera relative to the pointer 300.

In one or more examples, the pointer 300 can include one or more fiducial rings 308A-B located proximally of the tip 306. In the example of FIG. 3, the pointer 300 is illustrated as having two fiducial rings 308A-B however the number of rings shown in FIG. 3 is meant as an example only and should not be seen as limiting to the disclosure. In the illustrated example, the fiducial rings 308A-B are each configured as a polygonal ring that has a set of flat faces (also referred to as sides) arrayed about a longitudinal axis of a shaft or a portion of a shaft of the pointer tool. The flat faces can extend parallel to the longitudinal axis or transversely to it. A set of flat faces can include three or more flat faces. However, this configuration of a fiducial ring is merely exemplary. The fiducial ring may comprise a circular shape or any other shape suitable for displaying fiducial markers within the field of view of the camera. In one or more examples, a pointer can include less (i.e., one) or more fiducial rings than the two shown in FIG. 3. In one or more examples, fiducial rings 308A-B can include a plurality of faces (i.e., sides) with each side configured to have a fiducial marker disposed on it resulting in two sets of fiducial markers (one set is the fiducial marks on fiducial ring 308A and the other set is the fiducial markers on fiducial ring 308B). As will be described in further detail below, each fiducial marker can be used to identify the location of one or more geometric features of the pointer 300, and the location of the geometric features can be used to determine the position of the tip 306 of pointer 300 as described in detail below. In one or more examples, the number of faces of each fiducial ring can be selected such that at least one face of at least one fiducial ring 302A-B will be visible by a camera viewing the tool at any given time and at any given orientation of the pointer tool. In one or more examples, each fiducial ring (i.e., 308A-B) can be spaced apart from the tip 306 such that the fiducial rings are not located at the tip itself. In one or more examples, by disposing the fiducial rings apart from the tip 306, in the event that the tip 306 may be occluded (for instance by the patient's anatomy), it may still be possible to ascertain its position by using the fiducial markers which may still be visible in the endoscopic images/video feed.

In one or more examples, a first fiducial ring 308A can be disposed on the first portion 302 of pointer 300, while a second fiducial ring 308B can be disposed on the second portion 304 of pointer 300. In this way, first fiducial ring 308A can be aligned with axis 310, while second fiducial ring 308B can be aligned with axis 312, thus making the first fiducial ring 308A and second fiducial ring 308B angularly oriented with respect to one another. Thus, in one or more examples, the orientation of the fiducial rings with respect to one another can help to ensure that at least one face of a single fiducial ring is visible to the camera at any orientation of the tool in relation to the camera. As discussed in detail below, the faces of the fiducial rings can have one or more fiducial markers disposed on them that are configured to allow for the location of the tip 306 to be determined from an image of the tool. Thus, in one or more examples, ensuring that at least one face of at least one fiducial ring is visible to the camera at any given time may allow the tip of the tool to be located in any orientation of the pointer tool.

Figure 11:
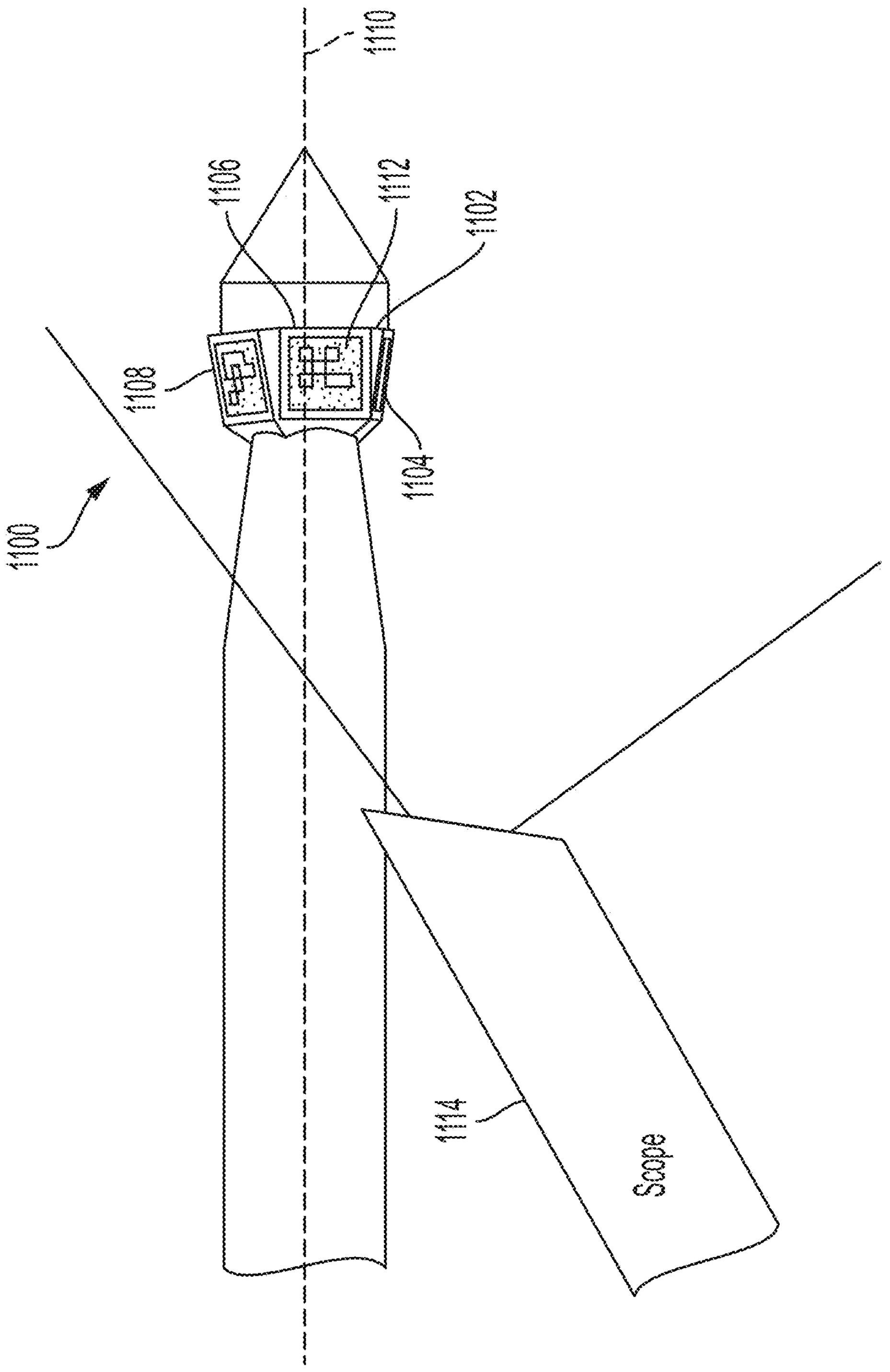
FIG. 11 illustrates another example of a pointer of the pointer tool according to examples of the disclosure.

FIG. 11 illustrates another example of a pointer of the pointer tool according to examples of the disclosure. In one or more examples, the pointer 1100 of FIG. 11 can represent an example of the pointer discussed above with respect to pointer 204 of pointer tool 200 of FIG. 2. Pointer 1100 includes a fiducial ring 1102 that has sides (e.g., three sides 1104, 1106, 1108 are shown) that extend transversely to the longitudinal axis 1110 of the pointer 1100 (which may also be the longitudinal axis of the shaft 202 of the pointer tool 200) in such a way that the sides 1104, 1106, 1108 face at least partially in a proximal direction. This orientation can help ensure that at least one fiducial marker 1112 disposed on the sides 1104, 1106, 1108 is visible by an endoscope 1114, which may be positioned alongside the pointer 1100. Although one fiducial ring 1102 is shown in the example of FIG. 11, other examples of pointer 1100 can include multiple fiducial rings 1102.

As described above, the fiducial rings that form part of the pointer can be configured to have one or more fiducial markers disposed on them that can aid an image processing tool to locate the precise location of the tip of the pointer tool in an image. In one or more examples, the fiducial markers can be used identify features of the pointer, that can be used to then locate the tip as described below. Since the shape of the tip may not lend itself to having a fiducial marker placed directly onto it, providing one or more fiducial rings on the pointer of the pointer tool can provide adequate surface area to place a fiducial marker. Additionally, the fiducial ring(s) can provide multiple surfaces to locate fiducial markers to help improve the accuracy of the tip location estimates as well as make the overall image processing algorithm used to detect the location of the tip robust to various orientations that the pointer tool can be placed in with respect to a camera.

Figure 4A:
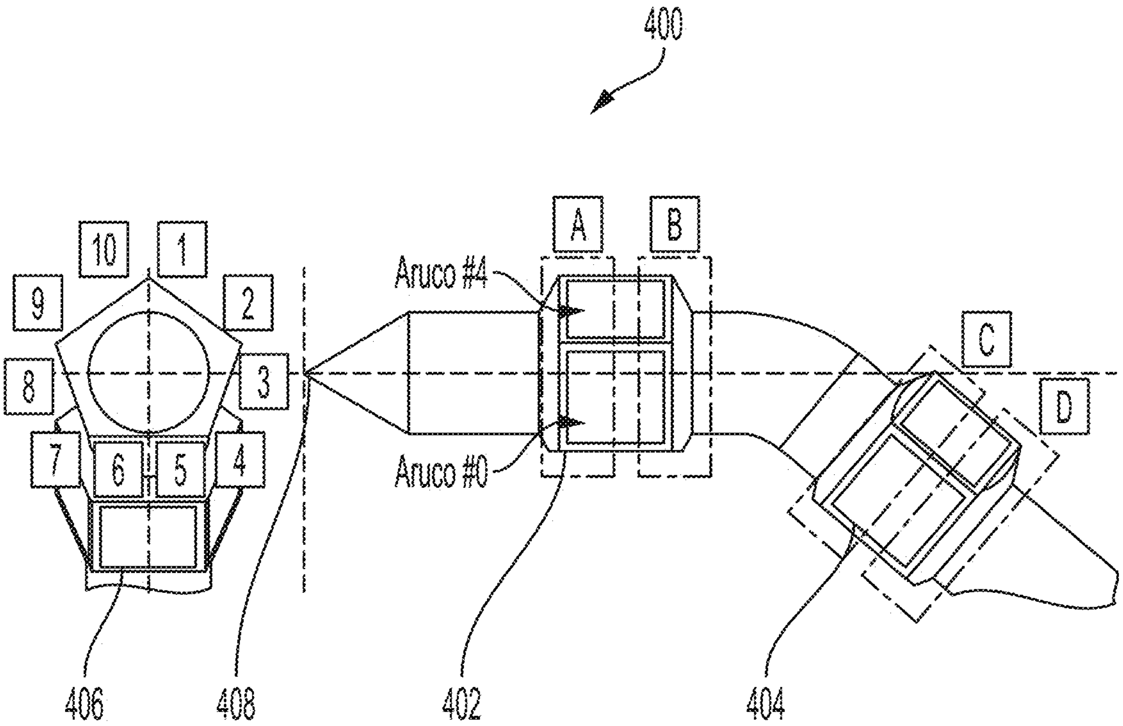

FIGS. 4A and 4B illustrate an exemplary placement of one or more fiducial rings of the pointer tool and corresponding tip locations according to examples of the disclosure. In one or more examples, the pointer 400 of FIG. 4A can include a first fiducial ring 402 and a second fiducial ring 404. The example of pointer 400 of FIG. 4A, while disclosing the placement of two separate fiducial rings, should not be seen as limiting, and in one or more examples, the pointer could include more or less fiducial rings than the example of FIG. 4A. Optionally, the first fiducial ring and second fiducial ring 402 and 404 can be angularly oriented with one another as described above with respect to FIG. 3.

In the example of pointer 400, the fiducial rings 402 and 404 can include five sides, thus making the fiducial ring a pentagon that is "wrapped around" the axis of the pointer that the fiducial ring is disposed on. Cross-section 406 illustrates a cross-sectional view of a fiducial ring. Cross-section 406 illustrates that the pentagonal shape of the fiducial ring includes five faces. In one or more examples, the five faces may collectively form two separate rings of 10 corners. In one or more examples, the 10 corners of a single ring are shown in cross-sectional view 406. In one or more examples, each fiducial ring 402 and 404 can form two rings of corners. For instance, fiducial ring 402 can form a first ring of corner labeled as "A" in the drawing, and a second ring of corners labeled "B" in the drawing. In one or more examples, and as shown by cross-sectional view 406, each ring of corners can include 10 separate corners, with each of the sides of fiducial ring having two corners per face. Likewise, fiducial ring 404 can also form two rings of 10 corners each labeled "C" and "D" in the figure.

In one or more examples, each corner of each ring of corners can have its distance from the tip 408 measured a priori so that anytime the location of a corner is determined in an endoscopic image, the location of the tip 408 can be automatically derived based on the a priori measured distance. In one or more examples, the distance from each corner to the tip can be empirically measured at the time of manufacture of the pointer tool. Thus, in one or more examples, when the tool is in use during a surgical procedure, an image processing system analyzing images that include the pointer tool can have beforehand knowledge about the distance relationships between each corner of the fiducial rings and the tip 408. The distance from a corner to a tip can be based on a three-dimensional (x,y,z) coordinate system in which the tip 408 of the pointer is assumed to be the origin (i.e., (0,0,0)). Thus, in one or more examples, the distance of each corner of the rings of corners can be measured in terms of displacement in a particular coordinate axis from the tip 408. Table 410 illustrates an exemplary table of distances for the corners of fiducial rings 402 and 404. Table 410 can include sections 412A-D, with each section representing a ring of corners associated with a fiducial ring. For instance, section 412A can represent the distances from each corner 1-10 of the ring of corners "A". Section 412B can represent the distances from each corner 1-10 of the ringer of corners labeled "B". Section 412C can represent the distances from each corner 1-10 of the ringer of corners labeled "C". Section 412D can represent the distances from each corner 1-10 of the ring of corners labeled "D".

Looking at an example entry of table 410, the ring of corners denoted as "A" and specifically corner "1" of ring A can have an (x,y,z) entry that represents the distance for each respective coordinate plane from the corner to tip 408. Thus, in the example of A-1, the corner can be 0.221763 inches away from the tip 408 in the X-direction, 0.069937 inches away from the tip in the Y-direction, and 0.012287 in the Z-direction. Thus, in one or more examples, if a three-dimensional location of a corner is determined (described in detail below), the entries in table 410 corresponding to the corner can be added and/or subtracted to the three-dimensional location of the corner to derive the location of the tip 408.

In one or more examples, the corners associated with each entry in table 410 are corners of a fiducial marker. In these examples, each (x,y,z) entry represents the distance from the respective corner of the fiducial marker to tip 408.

In one or more examples, a fiducial marker can be placed on each face of the fiducial rings in order to aid an image processing algorithm to determine the three-dimensional location of one or more corners associated with the fiducial rings. In the example shown in FIG. 4A, fiducial rings with corners are disclosed as an example feature that can be used to determine the location of the tip 408, however the example should not be seen as limiting. In one or more examples, the fiducial markers can be used to identify the location of any feature associated with the pointer tool that has a known three-dimensional distance from the tip 408 such that when the position of the feature is identified, a corresponding three-dimensional distance can be added and/or subtracted to the determined location in order to determine the location of the tip 408 as described above.

Figure 5:
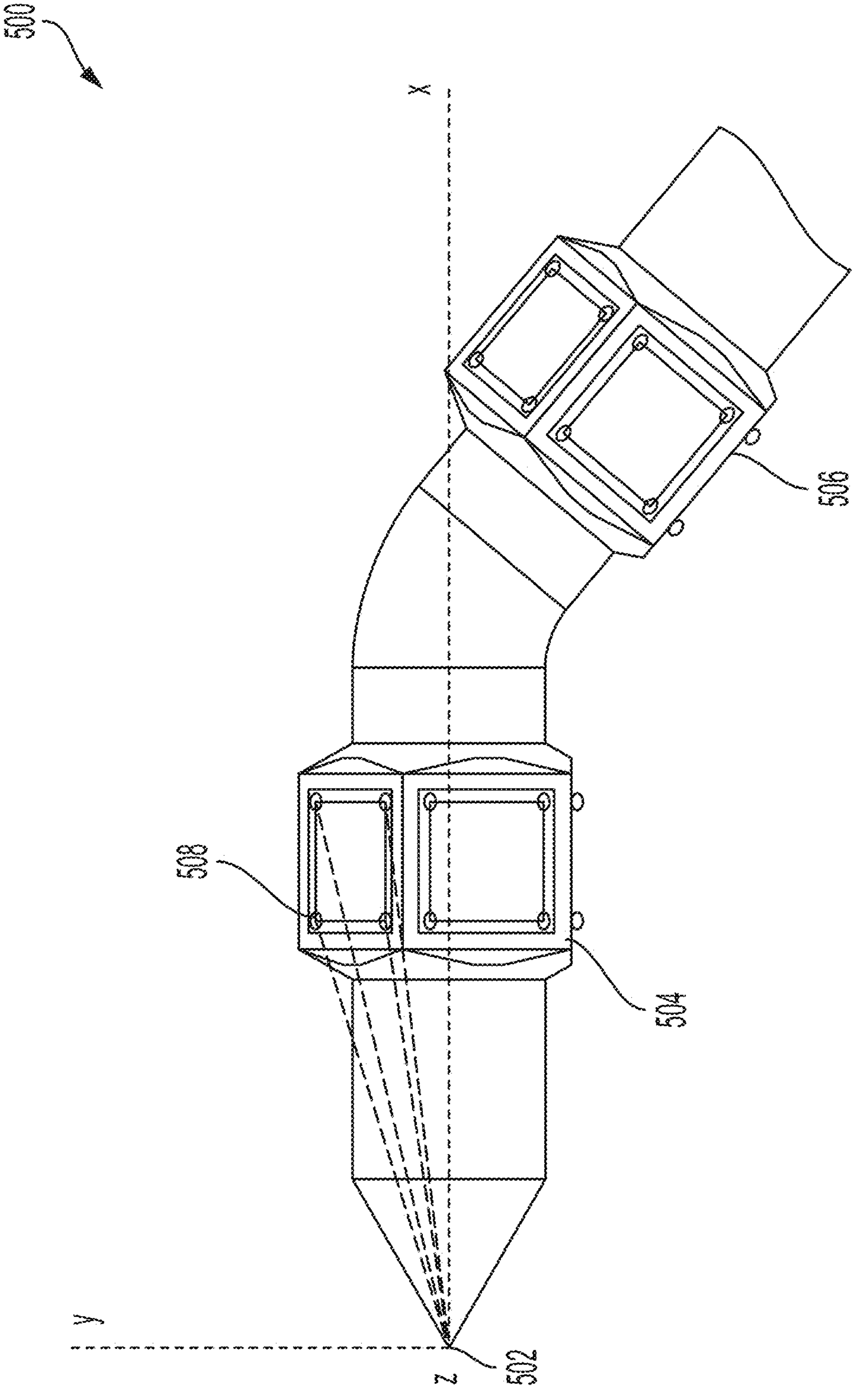
FIG. 5 illustrates an exemplary coordinate system for the pointer of the pointer tool according to examples of the disclosure.

FIG. 5 illustrates an exemplary coordinate system for the pointer of the pointer tool according to examples of the disclosure. In one or more examples, the pointer 500 of FIG. 5 includes a tip 502 and two fiducial rings 504 and 506. Each fiducial ring 504 and 506 includes a plurality of corners 508 similar to the corners described above with respect to FIGS. 4A and 4B. In the example shown in FIG. 5, the pointer 500 has been superimposed on a coordinate system to illustrate the operation of table 410 of FIG. 4B. In one or more examples, the tip 502 of the pointer 500 can represent the origin (0,0,0) of the coordinate system, and the coordinates of each of the corners 508 of the fiducial rings 504 and 506 represent the distance along the x-axis, y-axis, and z-axis (the z-axis is out of the page) from the tip. The example of FIG. 5 illustrates that if a three-dimensional location of any of the corners is determined, the location of the tip can be determined using table 410 which is pictorially depicted in FIG. 5. In some examples, the corners 508 are corners of the fiducial markers. For example, the fiducial markers may each have a square border and the corners 508 may be corners of the square border.

In one or more examples, each side (i.e., face) of a fiducial ring can have a fiducial marker disposed on it that can be used to not only identify the specific fiducial ring, but also to identify the particular face of the plurality of faces of the fiducial ring. The fiducial marker can provide the locations of the corners of the fiducial ring face or fiducial marker so that that the location of the tip can be ultimately determined as described above. In one or more examples, the fiducial markers disposed on each fiducial ring face can be an ArUco marker. As described in detail below, an ArUco marker can provide a visible pattern that can be efficiently found in an endoscopic image and can provide the information needed to uniquely identify the ArUco marker and, thereby, determine the two-dimensional and/or three-dimensional location in space of the tip of the pointer tool.

Figure 6:
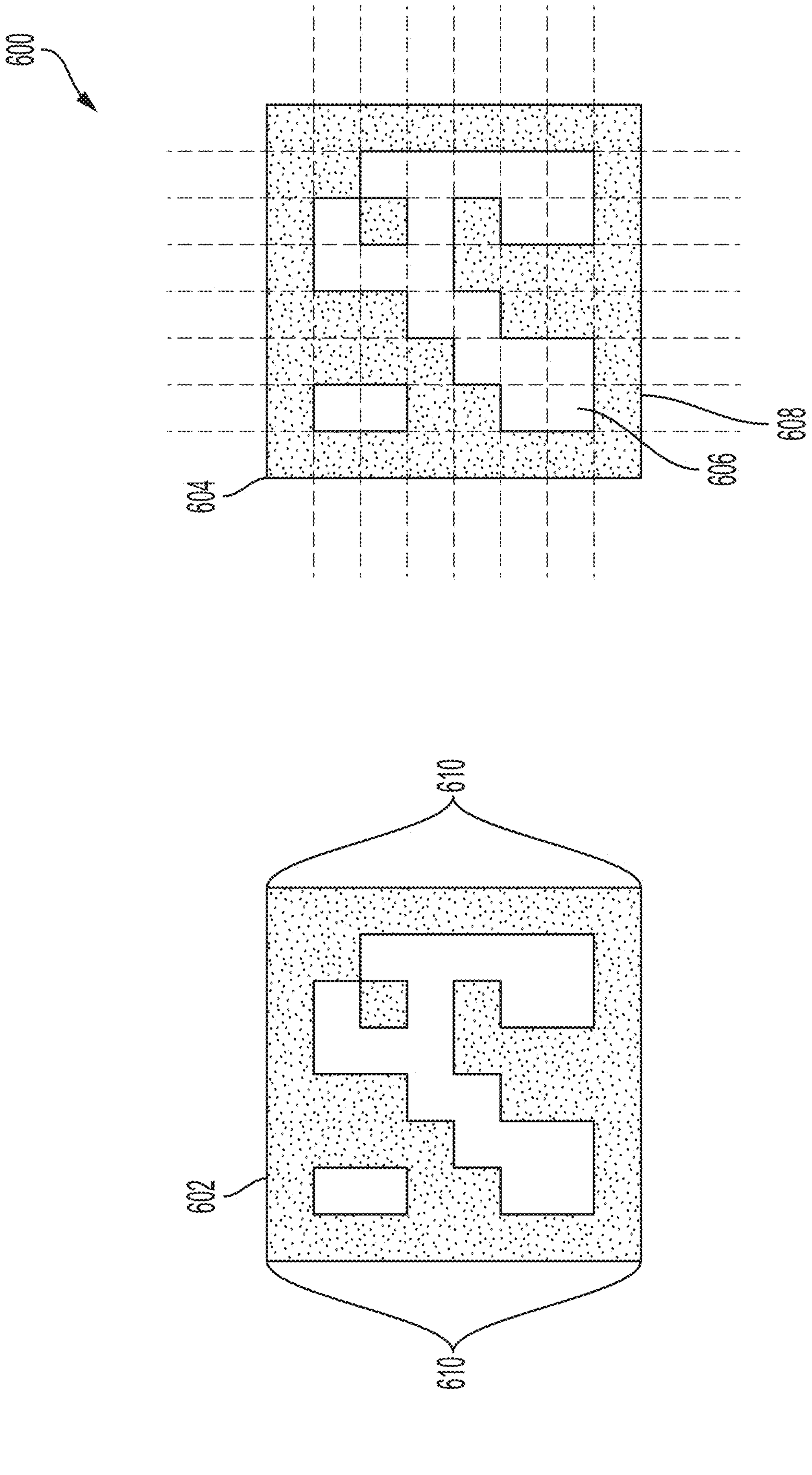
FIG. 6 illustrates an exemplary ArUco marker according to examples of the disclosure.

FIG. 6 illustrates an exemplary ArUco marker according to examples of the disclosure. In the example 600 of FIG. 6, an ArUco marker 602 can include a plurality of black and white blocks arranged in a specific pattern that allows the ArUco to not only be identified, but to also be distinguished from other ArUco markers. The blocks of the ArUco marker are arranged in a grid. For instance, ArUco marker 604 can represent the same ArUco marker 602 with a grid superimposed on the marker to better illustrate the plurality of blocks. In one or more examples, the ArUco marker 604 can contain 64 blocks that are arranged on an 8×8 matrix. In one or more examples, when viewing ArUco marker, an image processing system can extract coordinate values corresponding to the ArUco marker's four corner points (e.g., corner points 610 of ArUco marker 602), which enables calculation of the ArUco marker's location in three-dimensional space. Each ArUco marker on the pointer tool is unique and corresponds a distinct location on the pointer of the pointer tool. With the respective coordinates of the four corner points 610 known (relative to the pointer tip "origin"), the tip can be buried in tissue (not directly observed), yet its position in space also known. Other examples of fiducial markers that may be used are bar codes, Quick Response (QR) codes, glyphs, AprilTags, and/or any other fiducial marker suitable for providing location information in three-dimensional space.

In one or more examples, the ArUco marker 604 can include a border 608 that frames the ArUco marker 604 with a black border. In one or more examples, the border 608 can be disposed on the first row, the last row, the first column, and the last column of the marker. In the example of an 8×8 matrix, the border 608 can be arranged as described above to leave an internal 6×6 matrix. In one or more examples, each block 606 of the internal 6×6 matrix can have either a black or white block placed on it. The examples of an 8×8 matrix and 6×6 internal matrix are meant as examples only and should not be seen as limiting to the disclosure. Thus, in one or more examples, a particular ArUco marker can be configured in a variety of dimensions and grid layouts without departing from the scope of the present disclosure.

In one or more examples, the white and black blocks can be arranged on the 6×6 internal matrix to provide each ArUco marker with a unique pattern which can be used to uniquely identify each fiducial marker and, thereby, each face of each fiducial ring of the pointer tool. In one or more examples, an image processing system can determine the pattern of the blocks of the ArUco marker and obtain the location of the corners of the marker (i.e., the corners of the 8×8 matrix). The image processing system can use the determined pattern to extract the identity of the ArUco marker and can use the determined location of the corners to then find the location of the tip of the pointer tool based on a table correlating ArUco marker identities with locations of the corners of the ArUco markers relative to the tip of the pointer tool, as described above with respect to FIGS. 4 and 5. For example, the imaging processing system can access a table, such as table 410, that includes an (x,y,z) entry corresponding to each corner of each fiducial marker and can obtain the (x,y,z) entries for the corners of a given fiducial marker based on the identity of the fiducial marker extracted from its unique pattern of blocks. In one or more examples, the ArUco marker of a particular face can be used to determine the orientation of the pointer tool in the internal portion of the patient. Thus, not only can the marker be identified, but the positions of various portions (e.g., corners) of the marker can be determined to thereby determine the orientation of the pointer tool, which can represent further information that can be used to determine the location of the tip of the tool in the internal portion of the patient. In one or more examples, the ArUco markers can be laser etched on to each face of the fiducial rings. For example, the ArUco markers can be etched using a UV laser, a green laser, a fiber laser, and/or any other suitable laser etching process. In one or more examples, the ArUco markers are laser etched onto a black polymer material, such as a black Radel or black Delrin. In one or more examples, the ArUco markers may be laser etched onto a black anodized aluminum. In one or more examples, the ArUco markers may be UV laser etched onto black Delrin to achieve light colored blocks and dark colored blocks with high contrast and low reflectivity, which can improve detectability of the ArUco markers by an image processing system. Additionally or alternatively, the ArUco markers can be printed, machined, or affixed to the face of the fiducial ring using other processes and methods.

In one or more examples, the pointer tool described above with respect to FIGS. 2-6 can be specifically configured to allow for an image processing system to determine the location of the tip (in two and/or three-dimensions). Thus, in one or more examples, the features of the tool described above can be utilized during a process that can be used determine the location of the pointer. As an example, if a user indicates they wish to begin taking a measurement at the location where the tip of the pointer tool is located, then in one or more examples, an image processing system can initiate a process by which the system will acquire the location of the tip of the tool by searching for one or more of the fiducial markers disposed on tool and use the location of the markers to determine the location of the tip.

Figure 7:
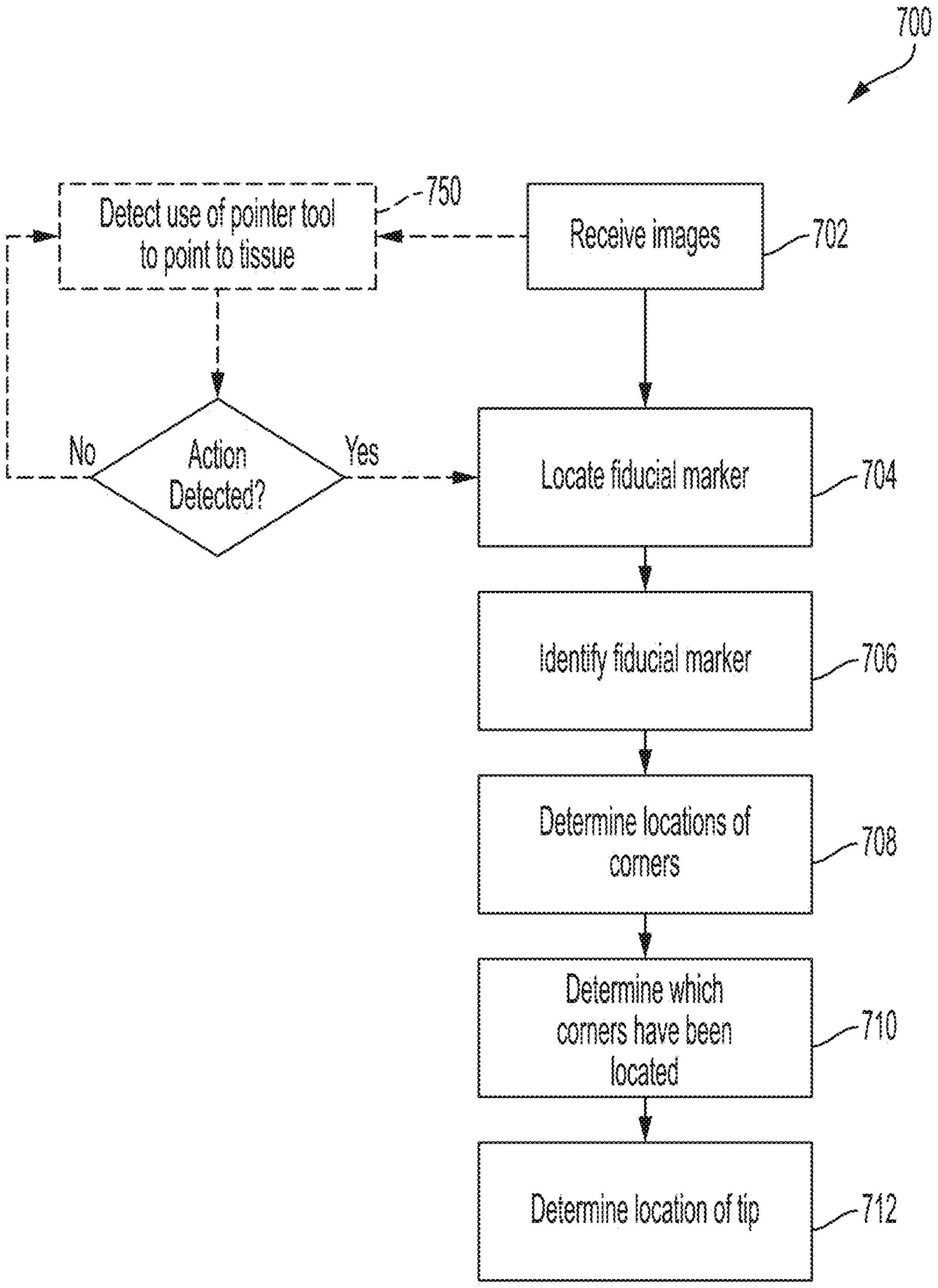
FIG. 7 illustrates an exemplary process for processing images containing a pointer tool according to examples of the disclosure.

FIG. 7 illustrates an exemplary process for processing images containing a pointer tool according to examples of the disclosure. In one or more examples, the process 700 of FIG. 7 can be initiated by a user of the pointer tool during a minimally invasive procedure. Additionally or alternatively, the process can be initiated periodically or without user initiation to determine the location of the tip of the pointer tool at any given time. In one or more examples, the process 700 of FIG. 7 can begin at step 702 wherein one or more images acquired from a medical imaging device (such as the one described above with respect to FIG. 1) are received at an image processing system, such as image processing unit 116 of FIG. 1.

At step 704, one or more of the fiducial markers of the pointer tool (described above) can be located within the image received at step 702. At step 706, the fiducial marker can be identified. As described above, in the case of an ArUco marker, identifying the one or more fiducial markers can include identifying one or more of the unique patterns (e.g., bit patterns) of the marker and determining the identity of the specific ArUco marker that is present within the image received at step 702 based on the identified pattern. In one or more examples, the image processing system performing the process 700 can access a look-up table that stores the association between ArUco markers and the specific faces of a fiducial rings that each pattern on the marker is associated with or the locations of the corners of the ArUco markers. In one or more examples, if the image processing system cannot identify any of the fiducial markers in an image, then the image processing system can apply one or more machine learning models to identify the pointer tool in an image and its orientation. Additionally or alternatively, fiducial markers may encode error detection and correction information such that any discrepancies and/or errors in detecting the bit pattern of the fiducial marker may be minimized to determine the correct information associated with a given fiducial marker.

In one or more examples, one or more machine learning models can be applied in parallel to and in combination with the process 700 of FIG. 7 in order to improve the accuracy of finding and identifying the fiducial markers with respect steps 704 and 706 described above. In one or more examples, a machine learning model can be used to segment the pointer tool from one or more images extracted from a video feed of the imaging device. In one or more examples, by segmenting the image (i.e., determining the contours of the tool from an image), an image processing algorithm can locate the portion of the segmented pointer tool where the fiducial markers may be, and can apply image processing techniques (i.e., such as adjusting the contrast or color of that portion of the image) so that the fiducial marker can be more easily found at steps 704 and 706 of process 700. Additionally or alternatively, a machine learning model can be used to find the location of the tip of the pointer tool in the image (i.e., by segmenting the tool from the image and locating the position of the tip) to serve as a check on the position of the tip determined by the ArUco markers, thereby improving the accuracy of the ArUco marker method for finding the tip (using the process 700 described above). In one or more examples, the video feed itself can have one or more machine learning models applied to it so that, for instance, any temporal aspects of the video can be used by the one or more machine learning models to segment the tool from an image and/or otherwise help to locate and identify the fiducial markers using the process 700 described above with respect to FIG. 7. In one or more examples, machine learning models can be trained using a supervised training process in which images or videos of the pointer tool are annotated with the precise location of the tool in the image, so as to train a machine learning model (for instance a convolutional neural network (CNN)) to recognize the presence and location of a pointer tool in a given image. In one or more examples, a machine learning model can be trained to analyze endoscopic video to detect the presence of a pointer tool in the video, determine a location of the pointer tool in the video, and track the pointer tool in the video over time. Such a machine learning model can be a convolutional long short-term memory (convolutional LSTM) model that utilizes both spatial and temporal features of endoscopic video and is trained in a weakly-supervised regime (e.g., where each label indicates a presence or absence of one or more pointer tools without providing their locations).

In one or more examples, both the process 700 as well as the machine learning model processes described above can be used to find the location of the tip in both pixel space (i.e., the (x,y) coordinates in the image where the tip is located) and/or three-dimensional space. In one or more examples, the process 700 can also determine the size of the fiducial marker, and use the determined size as a scale to generate measurements in the endoscopic image. Similarly, the segmented tool generated by the one or more machine learning models can also be used to determine the size of the tool in the image, which can then be used to generate a scale in the image that can be used to generate measurements in the endoscopic image.

Returning to the example of process 700 of FIG. 7, at step 708 the two-dimensional locations of corners of the fiducial marker in the image (e.g., in image space) are determined. At step 710, a determination is made of which corners have been located. This determination may be made based on the identity of the fiducial marker determined in step 706. For example, with reference to FIG. 4A, a determination may be made that the corners of previously identified ArUco #4 are corners associated with entries A-1, A-2, B-1, and B-2.

In one or more examples, at step 712, the location of the tip is determined based on the two-dimensional locations of the corners of the fiducial marker in the image and the determination of which corners have been located in step 710. In one or more examples, step 712 can include accessing a look-up table such as table 410 of FIG. 4B in which corners of each ArUco marker are listed, and each corner is associated with a corresponding distance to the tip (in the x,y,z axes) such that the distances from the corners to the tip can be combined (e.g., added and/or subtracted) with the locations of the corners to determine the location of the tip of the tool at step 712. As described above with respect to FIG. 4B, the table 410 can be determined and generated when the pointer tool is manufactured to ensure that the distances between each corner and the tip are accurately measured and used to populate the table prior to the pointer tool being used in a procedure.

As noted above, one or more machine learning models can be used in combination with one or more steps of process 700 of FIG. 7. In some examples, an image processing system, such as image processing unit 116 of system 100, uses a machine learning model to detect a particular use of a pointer tool that is indicative of a need to determine a position of a tip of the pointer tool and, in response to such a detection, to automatically initiate process 700 of FIG. 7. The machine learning model can be a deep learning model trained to simultaneously perform pointer tool tracking, rough localization of the tip of the pointer tool, and recognition of an action performed using the pointer tool. The deep learning model can be an "instrument-verb-target" model trained to process video to detect an instrument (e.g., a pointer tool), performing an action (e.g., pointing), with respect to a target (e.g., bony tissue of a joint). For example, the "instrument-verb-target" model may detect, in video, a pointer tool moving toward bony tissue of a joint and then stopping (e.g., for some period of time indicative of a pointing action by a user) and may determine that this activity of the pointer tool is indicative that the pointer tool is pointing to the bony tissue.

In some examples, an "instrument-verb-target" machine learning model can continuously process incoming video to detect use of the pointer tool to point to tissue. For example, referring to process 700 of FIG. 7, images received at step 702 can be processed by an "instrument-verb-target" machine learning model at step 750 to detect use of a pointer tool to point to tissue. The detection of such an action can then trigger performance of step 704, which is described in detail above.

In some example, the "instrument-verb-target" machine learning model can identify a region of the image containing the tip region of the pointer tool and the fiducial marker(s) and this information can be used in step 704 to reduce the amount of image data that is processed to locate the fiducial marker(s) in step 704, which can make locating the fiducial marker faster than processing an entire image. In other words, instead of step 704 including the processing of an entire image to locate the fiducial marker(s), processing may be limited to the region(s) of the image identified by the "instrument-verb-target" machine learning model. Optionally, one or more image enhancement techniques may be applied to the region(s) to improve the identification of the fiducial marker(s), which may also reduce the amount of processing relative to a process that applies image enhancement techniques to the entire image.

Although the above refers to the "instrument-verb-target" machine learning model detecting the use of a pointer tool, this is merely exemplary, and it should be understood that the "instrument-verb-target" machine learning model can be trained to detect the use of any tool, including, for example, a cutter, drill, or any other surgical tool. Additionally, the detection of a suitable action need not lead to (or only to) step 704. In some examples, a notification associated with the detection of the action can be provided to the user. For example, the detection of the use of a pointer tool can lead to a display, on a graphical user interface (e.g., GUI 1200 of FIG. 12A) of a function guide (e.g., function guide 1215 of FIG. 12A) that guides the user in using the pointer tool, for example, to define a measurement point. In some examples in which the tool detected is a cutter or drill and the target is tissue that should be avoided, an alert may be provided to the user alerting the user that the cutter or drill is too close to the tissue. An example of a suitable "instrument-verb-target" machine learning model usable in step 750 of FIG. 7 is described in Nwoye et al., Rendezvous: Attention Mechanisms for the Recognition of Surgical Action Triplets in Endoscopic Videos, arXiv:2019.03223v2 (Mar. 3, 2022), which is incorporated by references in its entirety. The machine learning model can be trained with video data in which frames of the video data are labeled with suitable "instrument-verb-target" labels. For example, frames of respective training videos that include a pointer tool that is being used to point to a bony structure of a joint can be labeled with "pointer tool-pointing-bony structure." The machine learning model can then be trained with such training videos to detect the use of a pointer tool to point to bony structure.

Referring back to FIG. 2, and as discussed above, the pointer tool 200 can include a controller 208 that can be configured to receive inputs from a user and transmit the inputs to an external computing device (such as a device that processes medical imaging data) via the cable assembly 210. In one or more examples, the controller 208 can be integrated as part of the handle of pointer tool, and include one or more components embedded within the handle of the pointer tool 200 that are collectively configured to receive a user's inputs and transmit them to an external computing device for processing.

Figure 8:
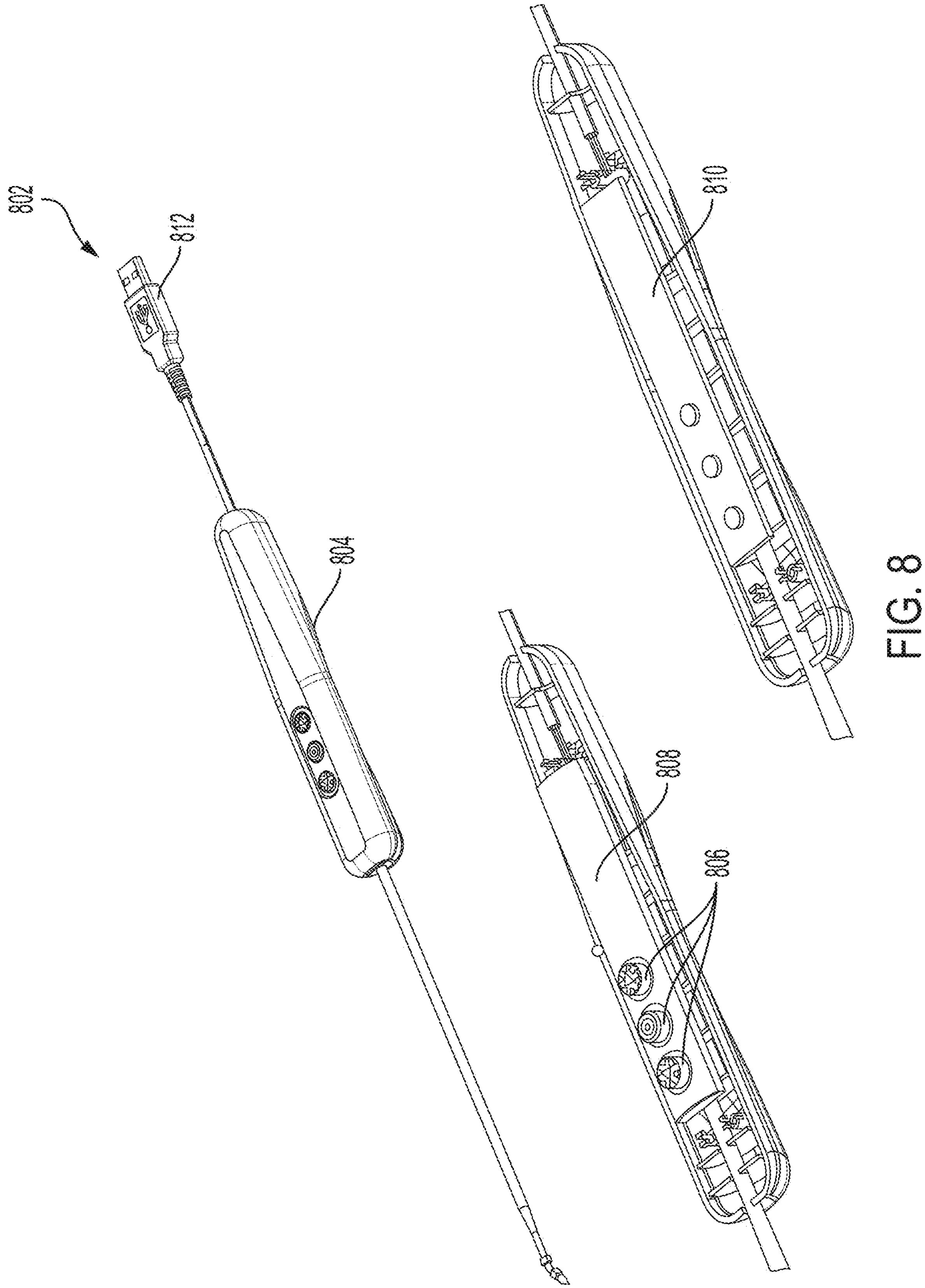
FIG. 8 illustrates an exemplary controller of the pointer tool according to examples of the disclosure.

FIG. 8 illustrates an exemplary controller of the pointer tool according to examples of the disclosure. In one or more examples, the pointer tool 802 can include a controller 804 that can not only be configured to receive a user's inputs, but can also serve as the handle of the tool. In one or more examples, the controller 804 can employ an ergonomic design such that the surgeon can comfortably grasp the controller during a surgical procedure to navigate the tool inside of the patient's internal anatomy during minimally invasive surgical procedure. In one or more examples, the controller 804 can include one or more buttons 806 that are collectively configured to receive a user's inputs. In one or more examples, the user can indicate the stop and start of measurement using the buttons 806 of the controller 804. In one or more examples, the controller 804 can include a protective silicone pad 808 that can protect a printed circuit board (PCB) 810 that is disposed underneath the silicone pad 808. In one or more examples, PCB 810 can include the electronic components that may be necessary to convert a user's physical button press into an electronic signal that can be communicated to an external computing device via a cable assembly 812 disposed on the end of the pointer tool 802. In one or more examples, the PCB can be configured to provide a message through the cable assembly 812 to an external computing device identifying the tool to the external computing system.

In one or more examples, instead of the pointer tool including a dedicated controller, the pointer tool can be inserted into an external controller that can be configured to operate with a variety of surgical tools. However, in such a scenario, the external controller may need to identify the tool that is inserted into it, so that it can translate the user's input appropriately to indicate the desired action initiated by the user pressing a button on the external controller. As an example, and with respect to the pointer tool, if a user pushes a specific button on the external controller to initiate a measurement, then in one or more examples, the controller recognizing that a pointer tool is plugged into it can either send a signal (e.g., to an image processing system) indicating the beginning of a measurement or can send a signal (e.g., to an image processing system) that includes the identity of the tool that caused the transmission (described below).

Figure 9:
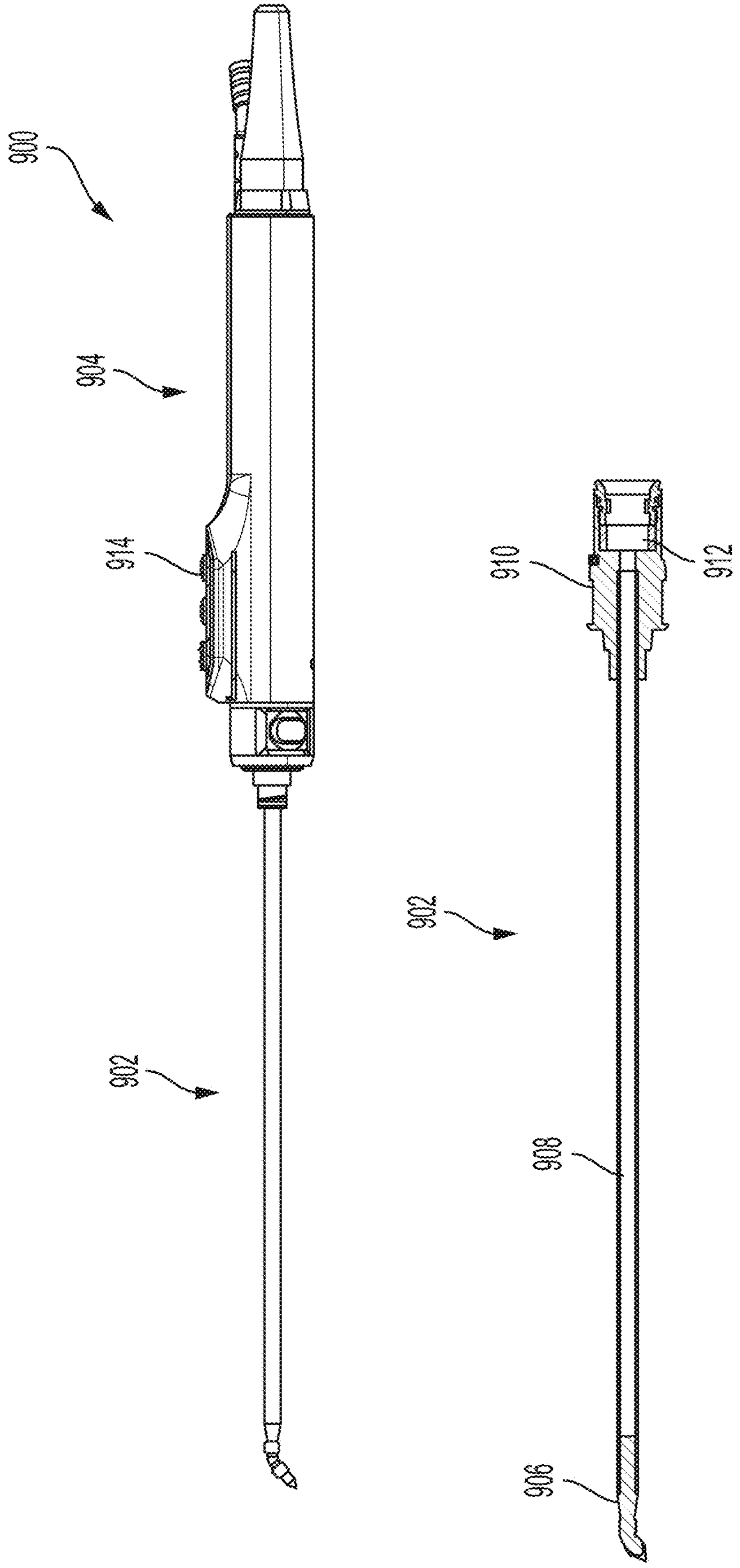
FIG. 9 illustrates an exemplary pointer tool interface to an external controller according to examples of the disclosure.

FIG. 9 illustrates an exemplary pointer tool assembly 900 that includes a pointer tool 902 interfaced to an external controller 904 according to examples of the disclosure. The pointer tool 902 can include a pointer 906 that includes the components (e.g., tip and fiducial markers) and arrangements discussed above with respect to FIGS. 2-6. The pointer tool 902 can also include a shaft 908 that is adhered to the pointer 906 or is machined from the same rigid piece of material as described above. The pointer tool 902 can include an interface 910 that is configured to interface with an external controller such as external controller 904. In one or more examples, interface 910 can be configured to mechanically interface with the external controller 904, such that the pointer tool 902 can be removably attached to the external controller 904. The external controller 904 can be configured as a handpiece and may include one or more buttons 914. Referring to system 100 of FIG. 1, the external controller 904 could be communicably coupled to a tool controller 126.

In one or more examples, in addition to being configured to mechanically interface with the external controller 904, interface 910 can also include one or more components that can identify the pointer tool 902 to the external controller 904 that it is connected to. For instance, in one or more examples, interface 910 can include a radio frequency identification (RFID) transmitter 912 that can transmit identification information stored in a memory to the external controller 904, allowing for the external controller 904 to determine that it is connected to the pointer tool 902. In one or more examples, the RFID transmitter 912 can transmit a signal to the external controller 904 to cause the external controller 904 to alter the function of the one or more buttons 914 located on the external controller 904 to reflect the operation of the pointer tool 902. The external controller 904 includes an RFID antenna, and an RFID signal received via the RFID antenna can be relayed to a connected system, such as tool controller 126 of FIG. 1. In this example, tool controller 126 may parse the RFID signal to determine that the pointer tool 902 is connected and, in turn, configure how the pointer tool 902 responds to user inputs to the one or more buttons 914 of the external controller 904 based on configuration data associated with operating the pointer tool 902. In one or more examples, the pointer tool 902 can be disposable such that it can be discarded after use in a surgery or other medical procedure. By having the external controller 904 be a separate device that can mechanically interface with the pointer tool 902, rather than being integral to the pointer tool 902, the pointer tool 902 can be made disposable more practically since the controller does not also have to be discarded and, thus, can be reused for other tools including additional pointer tools and/or cutting tools.

Figure 10:
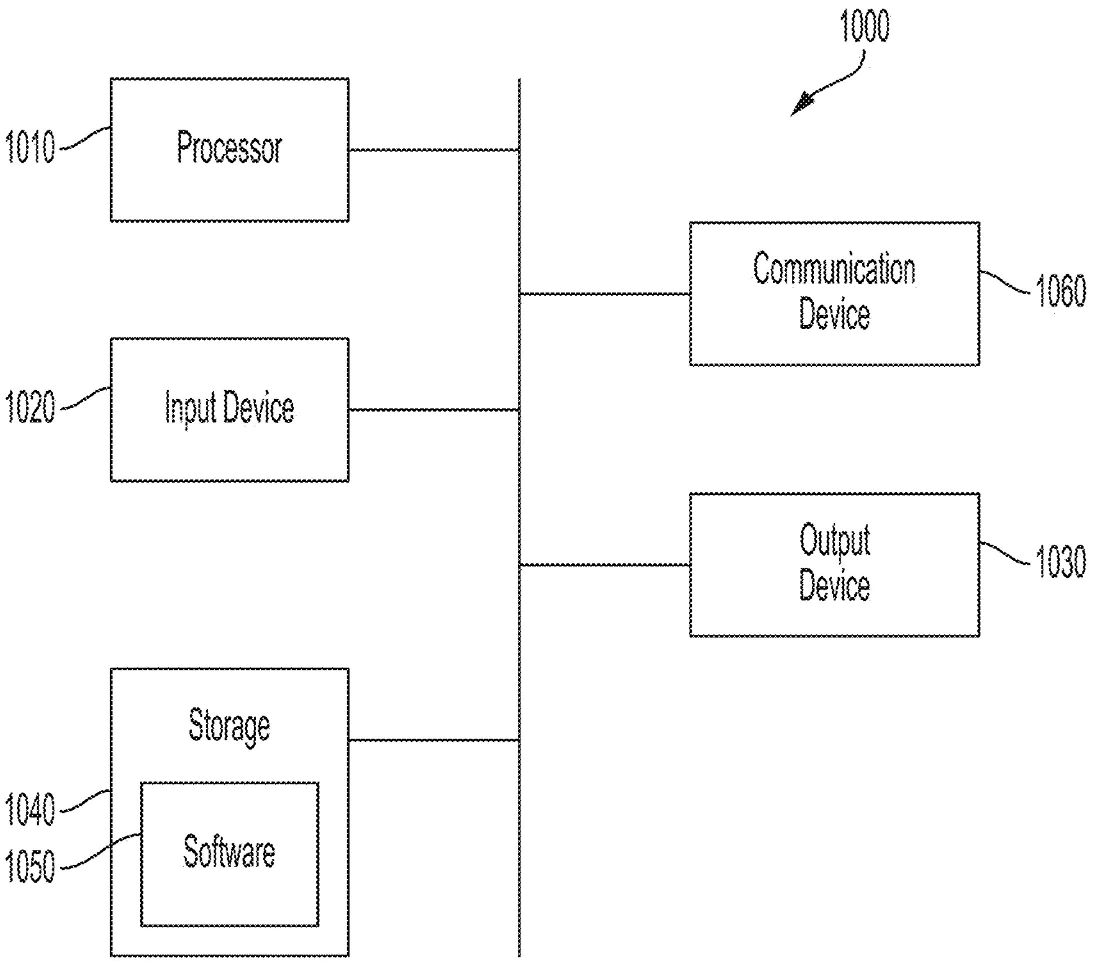
FIG. 10 illustrates an exemplary computing system, according to examples of the disclosure.

FIG. 10 illustrates an example of a computing system 1000, in accordance with some embodiments, that can be used for one or more of components of system 100 of FIG. 1, such as one or more of camera head 108, and camera control unit 112. System 1000 can be a computer connected to a network, such as one or more networks of hospital, including a local area network within a room of a medical facility and a network linking different portions of the medical facility. System 1000 can be a client or a server. As shown in FIG. 10, system 1000 can be any suitable type of processor-based system, such as a personal computer, workstation, server, handheld computing device (portable electronic device) such as a phone or tablet, or dedicated device. The system 1000 can include, for example, one or more of input device 1020, output device 1030, one or more processors 1010, storage 1040, and communication device 1060. Input device 1020 and output device 1030 can generally correspond to those described above and can either be connectable or integrated with the computer.

Input device 1020 can be any suitable device that provides input, such as a touch screen, keyboard or keypad, mouse, gesture recognition component of a virtual/augmented reality system, or voice-recognition device. Output device 1030 can be or include any suitable device that provides output, such as a display, touch screen, haptics device, virtual/augmented reality display, or speaker.

Storage 1040 can be any suitable device that provides storage, such as an electrical, magnetic, or optical memory including a RAM, cache, hard drive, removable storage disk, or other non-transitory computer readable medium. Communication device 1060 can include any suitable device capable of transmitting and receiving signals over a network, such as a network interface chip or device. The components of the computing system 1000 can be connected in any suitable manner, such as via a physical bus or wirelessly.

Processor(s) 1010 can be any suitable processor or combination of processors, including any of, or any combination of, a central processing unit (CPU), field programmable gate array (FPGA), and application-specific integrated circuit (ASIC). Software 1050, which can be stored in storage 1040 and executed by one or more processors 1010, can include, for example, the programming that embodies the functionality or portions of the functionality of the present disclosure (e.g., as embodied in the devices as described above)

Software 1050 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1040, that can contain or store programming for use by or in connection with an instruction execution system, apparatus, or device.

Software 1050 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport computer readable medium can include, but is not limited to, an electronic, magnetic, optical, electromagnetic, or infrared wired or wireless propagation medium.

System 1000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 1000 can implement any operating system suitable for operating on the network. Software 1050 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated. For the purpose of clarity and a concise description, features are described herein as part of the same or separate embodiments; however, it will be appreciated that the scope of the disclosure includes embodiments having combinations of all or some of the features described.

Although the disclosure, aspects, features, options, and examples have been fully described with reference to the accompanying figures, it is to be noted that various changes and modifications will become apparent to those skilled in the art. Such changes and modifications are to be understood as being included within the scope of the disclosure, aspects, features, options, and examples as defined by the claims. Finally, the entire disclosure of the patents and publications referred to in this application are hereby incorporated herein by reference.

The invention claimed is:

1. A tool for use in endoscopic surgical procedures, the tool comprising:

a shaft, wherein the shaft includes a first end, a second end, and a first axis; and a pointer at the first end of the shaft, wherein the pointer comprises:

a tip, and a plurality of fiducial markers disposed proximally of the tip, wherein a first set of fiducial markers is aligned with the first axis and a second set of fiducial markers is aligned with a second axis that is not parallel to the first axis, wherein at least one fiducial marker of the second set of fiducial markers is disposed on a surface that is coincident with a plane that intersects the first axis, wherein the surface is not parallel to the first axis, wherein the plurality of fiducial markers are configured for providing information for locating the tip of the pointer in an endoscopic image captured by an endoscopic imaging device.

2. The tool of claim 1, wherein the plurality of fiducial markers are ArUco markers.

3. The tool of claim 1, wherein each fiducial marker comprises a unique identifier that can be used to obtain a distance between one or more features of the fiducial marker and the tip.

4. The tool of claim 1, wherein the tool comprises a controller disposed at the second end of the shaft, and wherein the controller is configured to receive one or more inputs from a user of the tool.

5. The tool of claim 4, wherein the controller comprises one or more buttons that are configured to be pushed by the user to indicate a desired action.

6. The tool of claim 5, wherein the one or more buttons are configured to allow the user to navigate a graphical user interface displayed on an external display.

7. The tool of claim 4, wherein the controller is configured to provide a message through a cable to an external computing system identifying the tool to the external computing system.

8. The tool of claim 4, wherein the tool comprises memory storing information to identify the tool to the controller.

9. The tool of claim 1, wherein the first axis extends through the tip of the pointer.

10. A method for determining a location of a tip of a tool, the method comprising:

receiving an endoscopic image, wherein the endoscopic image comprises an image of the tool, and wherein the tool comprises:

a shaft including a first end, a second end, and a first axis, and a pointer at the first end of the shaft, wherein the pointer comprises:

the tip of the tool, and a plurality of fiducial markers disposed proximally of the tip, wherein a first set of fiducial markers is aligned with the first axis and a second set of fiducial markers is aligned with a second axis that is not parallel to the first axis, wherein at least one fiducial marker of the second set of fiducial markers is disposed on a surface that is coincident with a plane that intersects the first axis, wherein the surface is not parallel to the first axis;

determining an identity of at least one fiducial marker of the plurality of fiducial markers; and determining a three-dimensional location of the tip of the tool based on the determined identity of the at least one fiducial marker.

11. The method of claim 10, further comprising determining locations of corners of the at least one fiducial marker of the plurality of fiducial markers in the received endoscopic image, wherein the three-dimensional location of the tip of the tool is determined based on the locations of the corners.

12. The method of claim 10, wherein determining the identity of the at least one fiducial marker of the plurality of fiducial markers comprises:

determining a location of the at least one fiducial marker in the received endoscopic image;

determining one or more visual patterns of the at least one fiducial marker; and extracting the identity of the at least one fiducial marker based on the one or more visual patterns.

13. The method of claim 10, wherein determining the three-dimensional location of the tip of the tool based on the determined identity of the at least one fiducial marker comprises:

identifying at least one corner of a plurality of corners of the at least one fiducial marker; and determining a three-dimensional location of the at least one corner of the plurality of corners relative to the tip.

14. The method of claim 13, wherein determining the three-dimensional location of the at least one corner of the plurality of corners relative to the tip comprises:

accessing a look-up table comprising a list of the plurality of fiducial markers and a corresponding plurality of corners, wherein each entry pertaining to a corner in the look-up table comprises a three-dimensional location of the respective corner relative to the tip; and extracting the three-dimensional location of the at least one corner relative to the tip.

15. The method of claim 13, wherein the three-dimensional location of the tip of the tool is determined based on the three-dimensional location of the at least one corner of the plurality of corners relative to the tip.

16. The method of claim 10, wherein the first set of fiducial markers is arranged on a first fiducial ring and the second set of fiducial markers is arranged on a second fiducial ring.

17. The method of claim 16, wherein the first fiducial ring is aligned with the first axis and the second fiducial ring is aligned with the second axis.

18. A system for determining a location of a tip of a tool, the system comprising a memory, and one or more processors, wherein the memory stores one or more programs that when executed by the one or more processors, cause the one or more processors to:

receive an endoscopic image, wherein the endoscopic image comprises an image of the tool, and wherein the tool comprises:

a shaft including a first end, a second end, and a first axis; and a pointer at the first end of the shaft, wherein the pointer comprises:

the tip, and a plurality of fiducial markers disposed proximally of the tip, wherein a first set of fiducial markers is aligned with the first axis and a second set of fiducial markers is aligned with a second axis that is not parallel to the first axis, wherein at least one fiducial marker of the second set of fiducial markers is disposed on a surface that is coincident with a plane that intersects the first axis, wherein the surface is not parallel to the first axis;

determine an identity of at least one fiducial marker of the plurality of fiducial markers; and determine a three-dimensional location of the tip of the tool based on the determined identity of the at least one fiducial marker.

* * * * *